United States Patent [19]
Pollock et al.

[11] Patent Number: 5,629,498
[45] Date of Patent: May 13, 1997

[54] INTRAOPERATIVE TRACKING DEVICES AND PROCESSES

[75] Inventors: Richard A. Pollock, 5805 State Bridge Rd., Suite G-182, Duluth, Ga. 30136; Mahmood S. Kassam, Richmond Hill, Canada

[73] Assignee: Richard A. Pollock, Duluth, Ga.

[21] Appl. No.: 374,186

[22] Filed: Jan. 18, 1995

[51] Int. Cl.⁶ .................... G01G 19/40; G01G 19/22; A61B 5/00; B65D 51/16

[52] U.S. Cl. .............. 177/15; 177/25.11; 177/25.13; 177/25.19; 177/50; 177/126; 177/160; 177/244; 220/404; 206/363; 128/760

[58] Field of Search ................ 177/3, 15, 25.11, 177/25.13, 25.14, 25.17, 25.19, 50, 126, 145, 160, 229, 244, 253, 262, 245; 220/404, 909; 206/363; 128/760, 771

[56] References Cited

U.S. PATENT DOCUMENTS

| | | | |
|---|---|---|---|
| 502,265 | 8/1893 | Abercrombie | 177/160 |
| 2,741,450 | 4/1956 | Thayer et al. | 177/160 |
| 3,097,649 | 7/1963 | Gray | 128/760 |
| 3,146,944 | 9/1964 | Grippi | 128/760 |
| 3,367,431 | 2/1968 | Baker | 177/15 |
| 3,422,816 | 1/1969 | Robinson et al. | 128/296 |
| 3,587,583 | 6/1971 | Greenberg | 128/296 |
| 3,749,237 | 7/1973 | Dorton | 128/296 |
| 4,043,412 | 8/1977 | Rock | 177/25.11 |
| 4,114,601 | 9/1978 | Abels | 128/296 |

(List continued on next page.)

FOREIGN PATENT DOCUMENTS

| | | |
|---|---|---|
| 0073156 | 2/1983 | European Pat. Off. . |
| 54-128190 | 9/1954 | Japan . |
| 51-148993 | 12/1976 | Japan . |

OTHER PUBLICATIONS

"MultiPlex™ Series 100 Fluid Management System," Baxter Healthcare Corporation, Round Lake, Illinois 1988.

"Proposed Recommended Practices for Sponge, Sharp, and Instrument Counts," AORN Journal, vol. 61, No. 2, Feb. 1995, pp. 404–412.

"Supertag–RF Identification of Grouped Objects New Product Opportunity," British Technology Group Ltd., Dec. 1993, two pages.

"Bar Codes Obsolete," Automatic I.D. News, Jun. 1994, pp. 1, 32–33.

"Supertag or super-hype," Automatic I.D. News, date unknown, pages unknown.

*Primary Examiner*—Cassandra C. Spyrou
*Assistant Examiner*—Randy W. Gibson
*Attorney, Agent, or Firm*—James L. Ewing, IV; Kilpatrick & Cody, L.L.P.

[57] ABSTRACT

Automated tracking devices for counting, sorting, weighing, and containing articles, such as sponges that contain fluids from patients undergoing surgery. Devices according to the present invention employ a suspended container for receiving and sorting the articles. The cumulative weight of the container contents is sensed accurately and registered reliably after an appropriate settling period via a load cell structure which is aimed at eliminating bending moments and non-vertical force components imposed by the container and its contents. Automatic sensing of the presence of the container allows continuous, rather than solely end-point, fluid monitoring during the surgical procedures and allows this monitoring to continue as successive containers are changed during an operation. Appropriate warnings occur after a predetermined number of articles have been introduced into the container, in order to indicate that a container change is due. Automated accumulation and retention of the articles reduces handling and provides enhanced health-care personnel safety by reducing potential exposure to blood-borne pathogens. Disposable containers according to the present invention may accordingly be formed of flexible material such as plastomeric material, and thus manufactured, shipped, handled and stored efficiently and inexpensively.

46 Claims, 20 Drawing Sheets

U.S. PATENT DOCUMENTS

| | | | |
|---|---|---|---|
| 4,193,405 | 3/1980 | Abels | 128/296 |
| 4,205,680 | 6/1980 | Marshall | 128/296 |
| 4,244,369 | 1/1981 | McAvinn et al. | 128/296 |
| 4,295,537 | 10/1981 | McAvinn et al. | 177/15 |
| 4,343,316 | 8/1982 | Jespersen | 128/771 |
| 4,422,548 | 12/1983 | Chessman et al. | 206/370 |
| 4,449,538 | 5/1984 | Corbitt et al. | 128/760 |
| 4,478,332 | 10/1984 | Wiestmiller | 206/361 |
| 4,532,936 | 8/1985 | LeVeen et al. | 128/762 |
| 4,540,398 | 9/1985 | Barson et al. | 604/1 |
| 4,658,818 | 4/1987 | Miller et al. | 128/303.1 |
| 4,658,834 | 4/1987 | Blankenship et al. | 128/771 |
| 4,678,049 | 7/1987 | Gummere et al. | 177/245 X |
| 4,712,567 | 12/1987 | Gille et al. | 128/771 |
| 4,715,457 | 12/1987 | Amacher et al. | 177/50 X |
| 4,770,187 | 9/1988 | Lash et al. | 128/760 |
| 4,922,922 | 5/1990 | Pollock et al. | 128/760 |
| 5,031,642 | 7/1991 | Nosek | 128/771 |
| 5,139,299 | 8/1992 | Smith | 220/909 X |
| 5,148,940 | 9/1992 | Mendise | 220/404 |
| 5,160,062 | 11/1992 | Strawder | 220/404 |
| 5,167,343 | 12/1992 | Winfrey et al. | 220/404 |

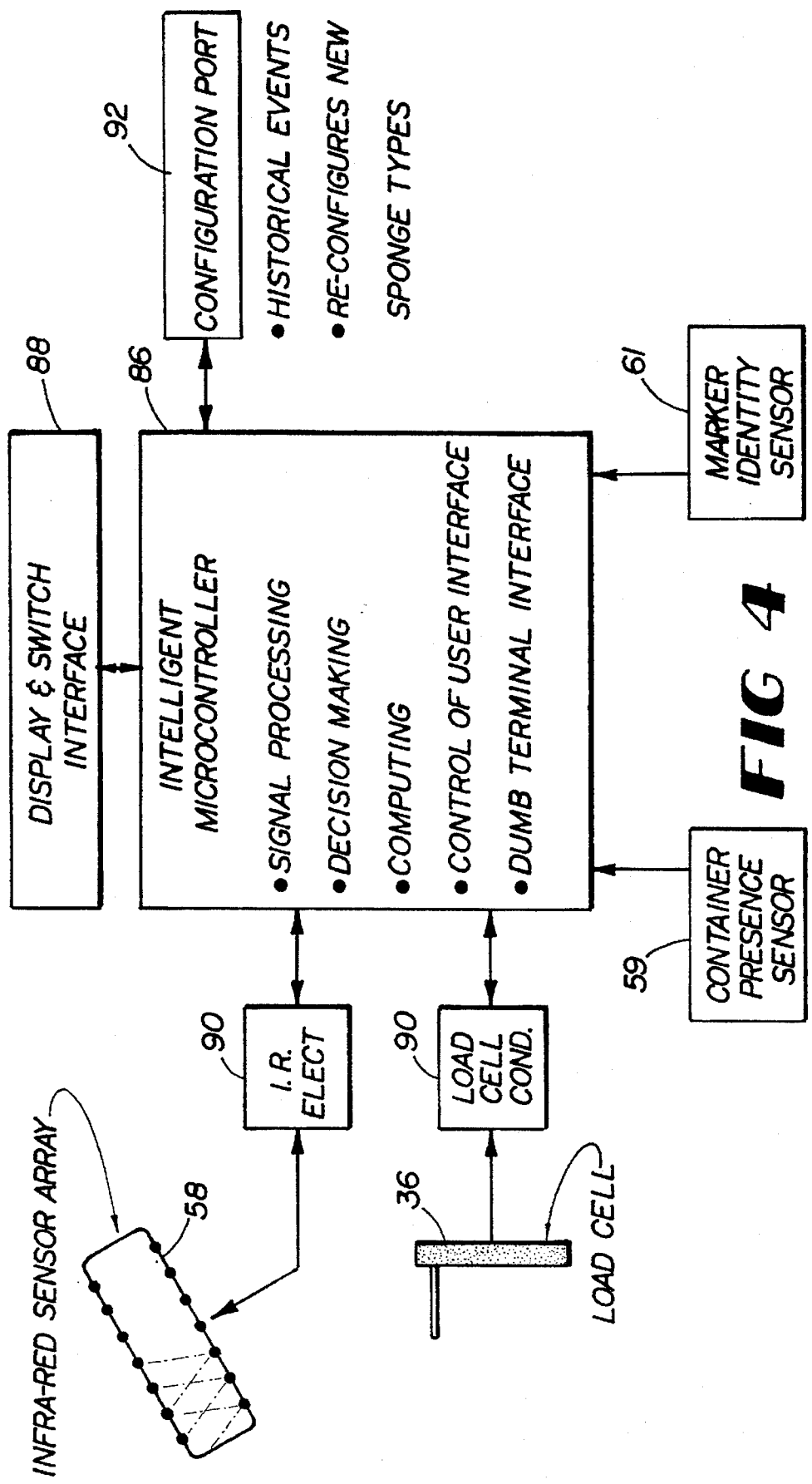

INTRAOPERATIVE TRACKING DEVICES AND PROCESSES

The present invention relates to devices and processes for tracking articles, such as sponges containing body fluids removed from patients during surgery.

BACKGROUND OF THE INVENTION

Tracking of body fluid loss during surgery is still done largely manually, as is accounting for sponges which have been utilized to absorb body fluids. Fluid loss must be tracked continually during a procedure in order to avoid underestimating (or overestimating) the number of units of blood or other fluid that must be administered to a patient for replacement of the lost fluid. Underestimation and overestimation carry attendant risks that are well known in the field.

Conventional fluid tracking techniques require that sponges containing body fluids be laid out on a fabric or plastic sheet or otherwise arranged in plastic bags or pockets where they can be inspected, sorted, counted, and contained for disposal. This handling task typically and ultimately falls upon the circulating nurse. The anesthesiologist or anesthetist visually estimates the quantity of blood and fluid in the sponges. The anesthesia staff typically simply look at the sponges and make their best estimate.

Conventional estimation of bodily fluid loss from sponge examination is accordingly an anachronism. Conventional wisdom holds, for instance, that anesthesiologists and surgeons tend to underestimate blood loss in the sponges. This is in great part due to the limited access to (and visibility of) the contaminated surgical sponge and to the dilution of the blood in the sponge by irrigant or body fluids. Evaporation of the sponge contents into the operating room air and absorption of fluids by surrounding materials (such as surgical drapes) further confuse the estimate.

Apart from fluid tracking issues, an accurate sponge count at the end of surgical procedures is also necessary in order (among other things) to ensure that no sponges have been left in the patient. Accordingly, sponges are conventionally counted manually during and at the end of a surgical procedure by the circulating nurse. Sometimes multiple counts are required for comfort and accuracy. The acts of counting and accounting require considerable handling, thus increasing the risk of transcutaneous biocontamination.

Blood and other body fluids have recently been considered to be biocontaminants that require careful handling, management and control because of the viral, bacterial, and other infectious agents they may contain. Laying the sponges out on plastic floor-sheets to account for blood loss, like other earlier techniques, is thus increasingly considered to be unacceptable. It is becoming more and more desirable in addition to dispose of items or articles, such as sharps and sponges, used during invasive procedures, in specifically marked, biohazard containers. Such containers have fluid-tight seals that limit the risk of contamination of the nurse or other user.

Devices for tracking body fluid loss and for displaying sponge counts during surgical procedures are available in the marketplace. U.S. Pat. No. 4,449,538 issued May 22, 1984 and entitled "Medical-Electronic Body Fluid Accounting System" and U.S. Pat. No. 4,922,922 issued May 8, 1990 to Pollock, et al. for a "Fluid Monitoring Apparatus" (both are incorporated herein by this reference) disclose devices that more accurately and safely monitor blood and body fluids in a patient. One device disclosed in the Pollock, et al. patent, for instance, employs a load cell that supports a container for receiving various sizes of sponges that contain such fluids. The sponges may be sorted by passing them through a disposable sorting grid located above, or forming a part of, a receptacle. Photoelectric or other sensors detect the cumulative number of sponges placed into the container via each opening in the sorting grid. The load cells and sensors are connected to controller circuitry. The controller counts, tracks, and displays the cumulative number of sponges of each size that pass the sensors and fall into the container; this controller also tracks the cumulative weight and calculates (using standard weight-to-volume ratios) and displays the cumulative volume of fluid in the sponges.

The use of a container that simply rests atop a surface supported by a number of load cells, such as those disclosed in the above-referenced Pollock, et al. patent, creates weighing inaccuracies, however. Malposition of the container on the surface, movement of the container (as sponges are placed in it or as the apparatus is moved during surgery), and the inherent plurality of the load cells are among the causes of such inaccuracies.

Additionally, a flexible container, such as a bag or other flexible receptacle that may be inexpensively manufactured and conveniently provided to receive the sponges, would be more desirable than the rigid receptacle first proposed. Such flexible receptacles would obviously collapse if placed atop a platform (such as shown in the above-referenced patent). Further, when rigid structure was added to the platform, ensuring that the receptacle would remain upright, the device became difficult to clean and maintain, and ultimately unsafe.

In order to decrease the potential for errors in the weighing, counting and tracking process and for initiating clinical malresults, human intervention should be minimized. For instance, it would be desirable to have the device automatically detect the presence or absence of a sorting receptacle, so that the apparatus could automatically tare the weight of the container without being instructed to do so by the human operator. Similarly, it would be preferable to have apparatus that automatically detects when one container has been removed and another replaced, rather than depending on the operator to push a button or sequence of buttons in order for the apparatus to recognize that removal or replacement has occurred. It would further be preferable to have the apparatus sense a blockage of the sensors, or detect the existence of other abnormal conditions, allowing the informed user to make necessary corrections to the tracking, sorting, and counting and weighing data. The desirability of automated apparatus functions is magnified when one considers the stressful and hurried environment characterized by some surgical procedures.

SUMMARY OF THE INVENTION

The present invention provides devices and processes for tracking surgical sponges or other articles, such as those utilized to absorb body fluids during and immediately after surgery. A flexible receptacle or other suspended structure, that may be inexpensively manufactured and efficiently folded, packaged, shipped and provided, is desired to retain the contaminated sponges. That receptacle is suspended from the device via a loadcell structure, preferably via a parallelogram-based load cell. The load cell is designed to minimize bending moments and nonvertical force components, in order to weigh the receptacle and its contents accurately.

The container preferably consists of a disposable (plastic) bag suspended from a rigid top member (disposable grid)

that contains one or a number of sorting-and-counting ports. Each port in the disposable grid varies in size and corresponds to a particular sponge size or type. The disposable container is adapted to detect articles by sensing their interruptions of energy emitted by photodiodes, phototransistors or other sensors in the rigid support frame that suspends the receptacle. Regions within the plastic bag or receptacle may be at least partially transparent; indeed, the entire bag or receptacle may be at least partially transparent in order to allow visual inspection of the sponges it contains. The receptacle is preferably divided into a number of sections, each corresponding to a port in the sorting grid, so that, for instance, smaller sponges passing through a first port may be contained in a separate section of the receptacle for easier visual inspection and visual double checking. The container preferably features a lid which may seal the ports of the sorting grid and the container. The lid provides adequate and sufficient protection from biohazards (such as viruses within the blood, on the sorting grid, on the flanges of the ports, or in the sponges) and offers compliance with certain biohazard regulations.

The device preferably automatically senses the presence or absence of the container suspended on its structure. Accordingly, the operator may simply start the device by placing the container receptacle in the rigid frame and by introducing articles, without the need to actuate switches or buttons. Similarly, the device automatically senses the removal of a first container and automatically senses introduction of additional containers during a surgical procedure, so that it may store the cumulative sponge counts and the cumulative weights of fluid in the first container, hold the data in memory, tare the weight of the second or subsequent containers, and reactivate the counting and weighing process automatically. This automated operation reduces the potential of human error in the weighing, counting and tracking process.

The device preferably automatically senses blockages of the ports by sponges or other articles, as well as other abnormal conditions. It notifies the user of such conditions and adjusts or corrects data associated with the tracking, counting, and weighing as necessary.

For accuracy and reliability, the device preferably allows a stabilization period after passage of an article through a port before registering a weight for the article, in order to allow the load cell to stabilize. Furthermore, the sensors for detecting the articles may be pulsed in bursts rather than operating continuously for more efficient and reliable detection of the passage of articles.

It is accordingly an object of the present invention to provide tracking devices and processes which allow use of flexible, potentially disposable, receptacles that may be easily and inexpensively manufactured, packaged and provided.

It is an additional object of the present invention to provide tracking devices and processes which sense automatically the presence or absence of the container within the device, thus eliminating or reducing the potential of human error in the cumulative weighing, sorting, counting, tracking, and containing process.

It is an additional object of the present invention to provide tracking devices and processes which detect sensor blockage by articles and then to notify the user of the abnormal conditions and to correct data relating to tracking and counting based on the blockage.

It is an additional object of the present invention to provide tracking devices and processes that suspend each container of tracked articles (that in turn contain varying amounts of fluids) and to weigh them more effectively by minimizing bending moments and nonvertical force components upon the load cell.

It is an additional object of the present invention to provide tracking devices and processes which employ a parallelogram-like load cell structure with a suspended container in order to allow more accurate and reliable cumulative weighing, counting and tracking of articles and the fluids within.

It is an additional object of the present invention to provide tracking devices and processes which register weight of articles after the load cell has settled in order to reflect accurate cumulative weight.

It is an additional object of the present invention to provide tracking devices and processes that employ pulsed photodiodes or phototransistors in order to sense the passage of articles more accurately.

It is an additional object of the present invention to provide tracking devices and processes which may include components that detect transmitters, transponders, or other identity markers, emitters or receivers in or on the articles and thus identify individually the tracked articles and their features, characters, identity, composition, nature, or source of distribution and manufacture (if desired) through one or more ports.

It is an additional object of the present invention to display in real time cumulative counts and cumulative fluid volumes (calculated by controller circuitry from cumulative weights).

It is an additional object of the present invention to allow manual adjustment by the operator of any sorting or counting errors.

It is an additional object of the present invention to reduce handling of sponges and other articles contaminated by blood-borne viruses or other pathogens and to provide a disposable container for their safe disposal.

It is an additional object of the present invention to allow the automated storage and transfer of tracking data within or beyond the operating room, to include but not limited to postoperative patient care centers, surgical recovery units, cost analysis and charge accounting units, anesthesia monitoring stations, hospital purchasing or supply, manufacturers, or waste-management and infectious disease control monitoring agencies.

It is an additional object of the present invention to allow the tracking and accounting of articles whether synthetic or cotton, woven or unwoven, small or large, strung or not.

Other objects, features and advantages of the present invention will become apparent with reference to the remainder of this document.

BRIEF DESCRIPTION OF THE DRAWINGS

FIG. 4 is a block diagram of the intelligence of the device shown in FIG. 1.

DETAILED DESCRIPTION OF THE DRAWINGS

Figure 1:
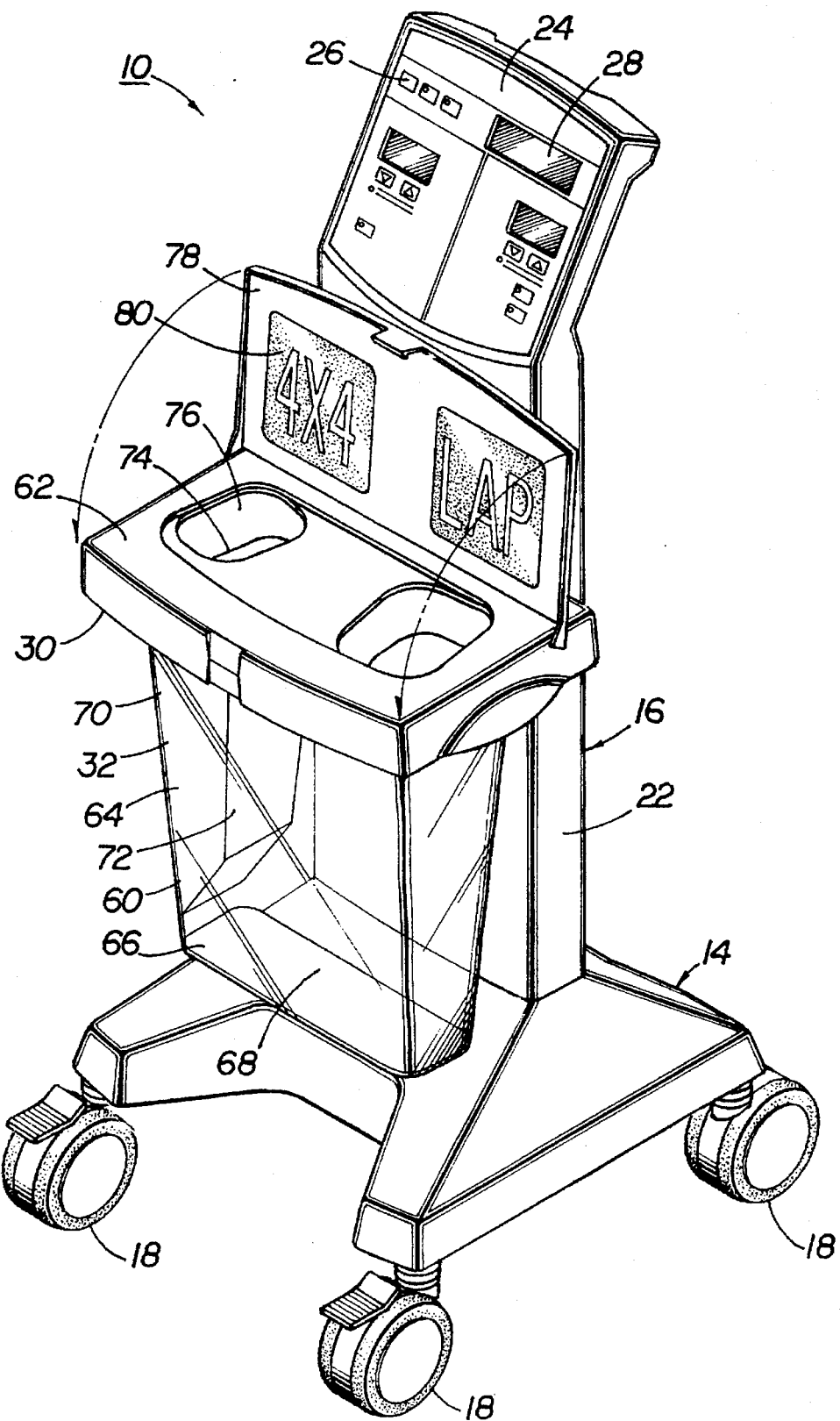
FIG. 1 is a perspective view of a first embodiment of a device according to the present invention.

FIG. 1 is a perspective view of a preferred embodiment of a tracking device 10 according to the present invention. FIG. 1C shows the device without certain facing. Briefly, device 10 includes a frame 12 which in turn includes bottom structure 14 and generally upright structure 16. Bottom structure 14 may be attached to a number of suitable casters, rollers or other means for allowing device 10 to be moved easily. Casters 18 (which may feature locks as shown) are attached in conventional fashion to bottom structure 14. Frame 12 may be formed of any desired metallic, plastomeric or other desired structural material 20 and have a facing 22 formed of plastomeric or other desired material which may be colored and shaped as desired.

Figure 1A:
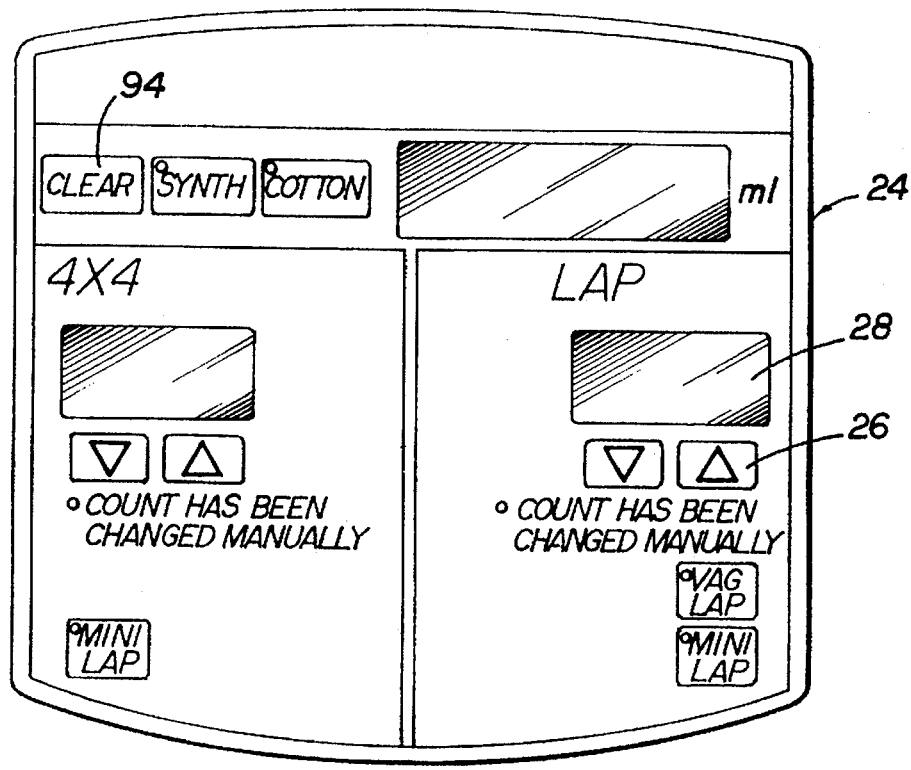
FIG. 1A is a plan view of a user panel according to one embodiment of the present invention for tracking two types of articles.
Figure 1B:
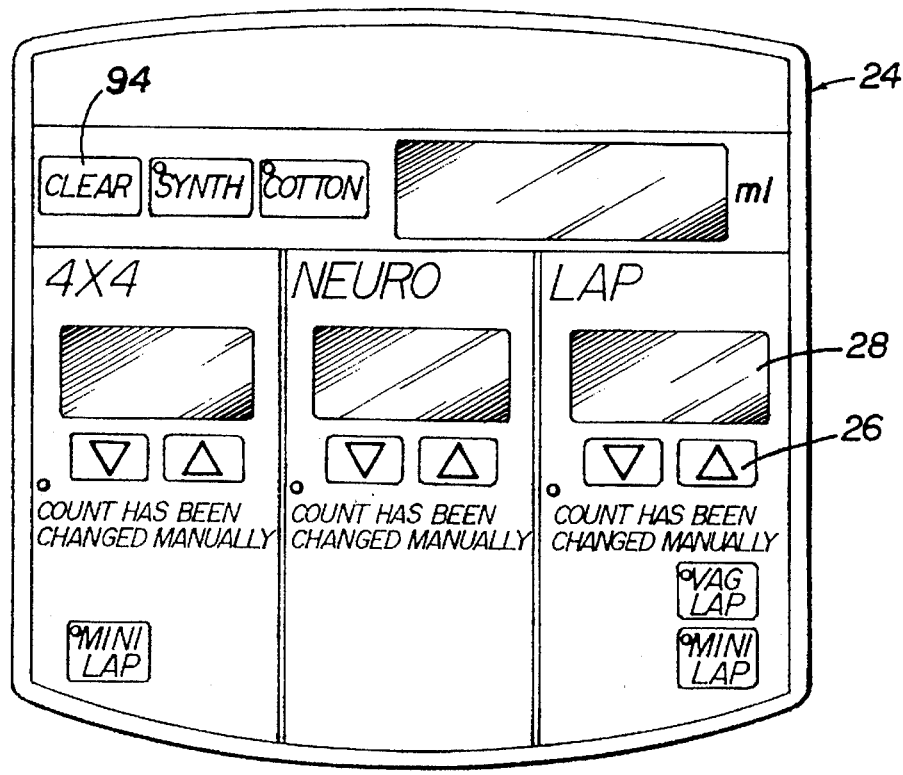
FIG. 1B is a plan view of a user panel according to one embodiment of the present invention for tracking three types of articles.
Figure 1C:
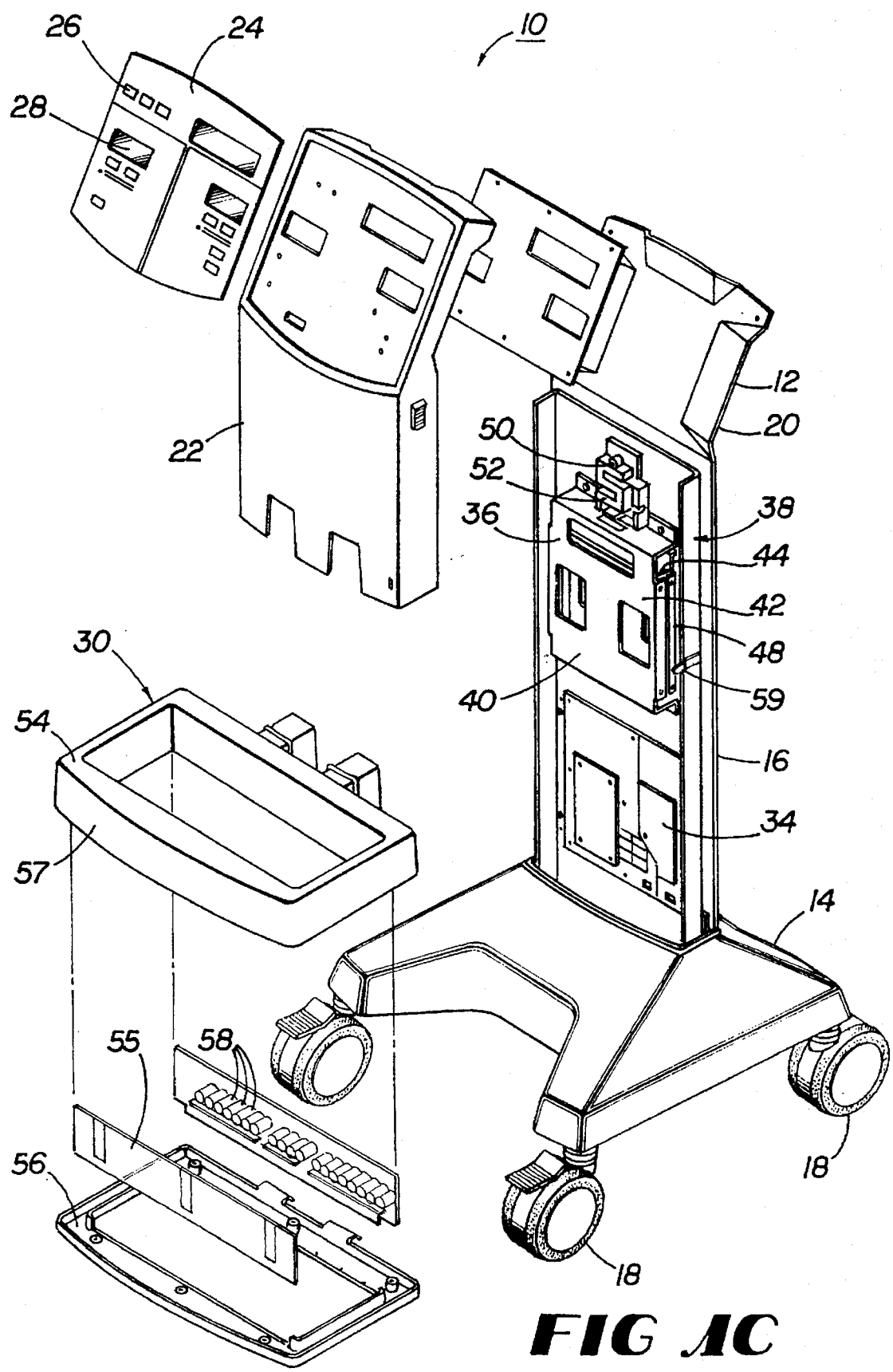
FIG. 1C is a perspective view of the device of FIG. 1 in which certain facing has been removed.

Frame 12 also includes, preferably at its upper portion as shown in FIG. 1, and in FIGS. 1A and 1B, a user interface and display panel 24 which contains a number of buttons or switches 26 and indicators 28. Buttons may be membrane or as otherwise desired. Indicators 28 may be liquid crystal diode, light emitting diode, incandescent or other suitable components for displaying information generated by device 10.

Figure 2:
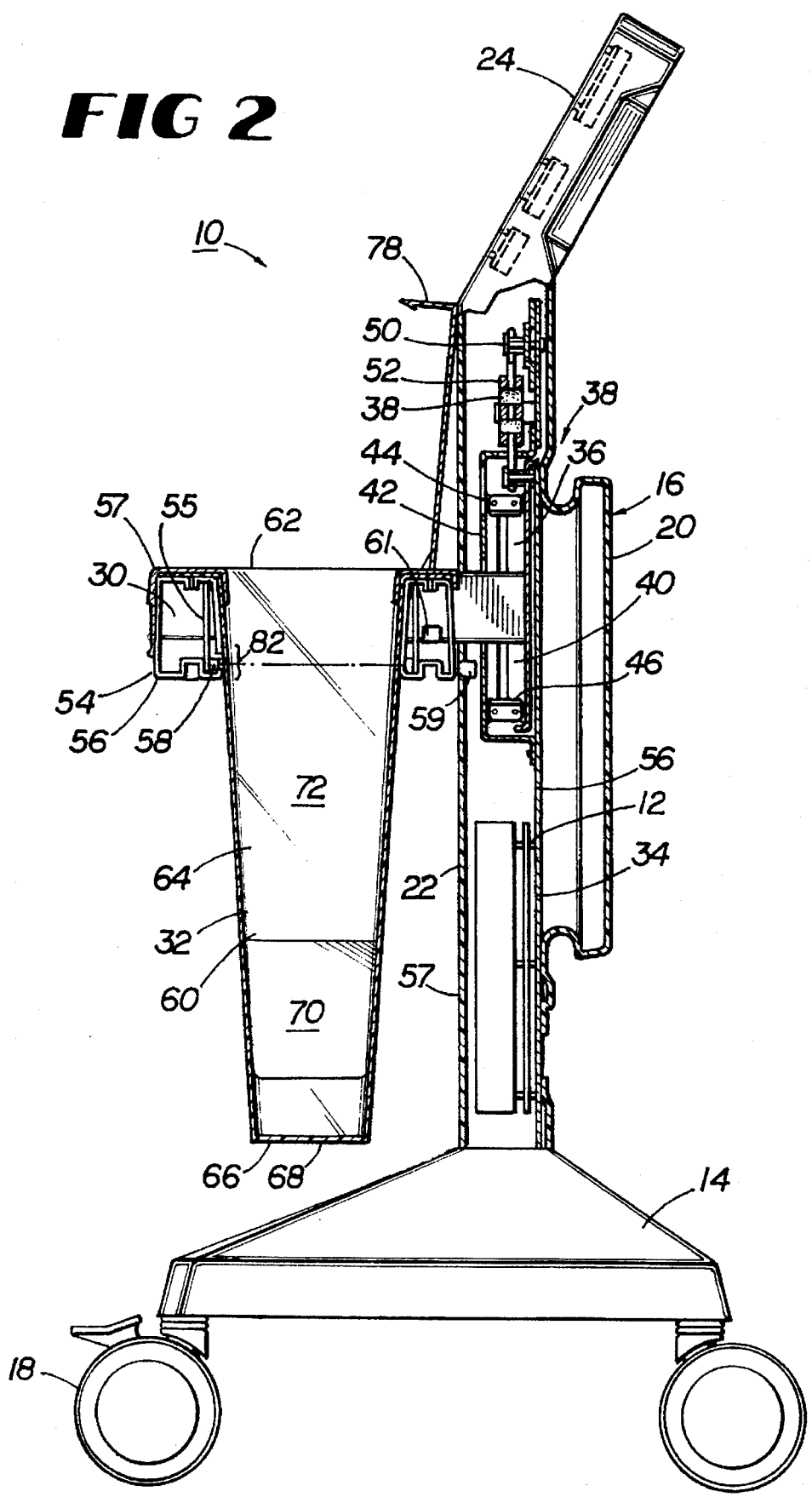
FIG. 2 is a schematic cross-sectional view of the device of FIG. 1.
Figure 2A:
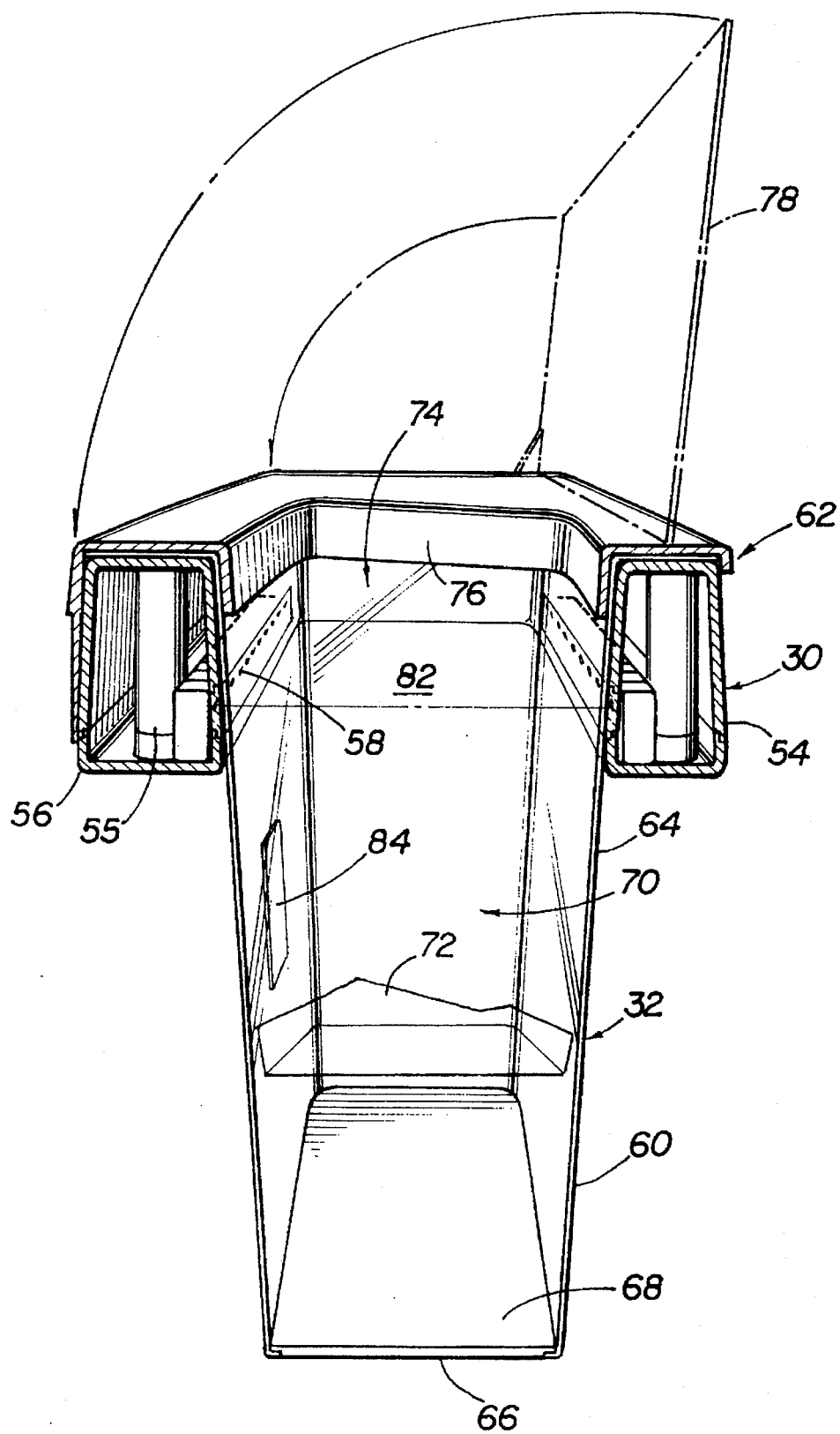
FIG. 2A is a partial cross sectional, partial perspective view of a preferred embodiment of a container according to the present invention.

As shown in FIGS. 1 and 2, extending from frame 12 is a rigid frame structure 30 for supporting a container 32. Container 32 is adapted to sort and/or receive articles such as sponges utilized in surgical procedures as discussed more fully below.

Device 10's frame 12 also mounts one or more circuit boards 34 which contain conventional processors, read only memory, random access memory, mass memory and input/output devices which communicate with components of the user panel 24, frame structure 30 for supporting the container, sensors 58 which sense articles in the container and marker detectors 59 as discussed more fully below. The circuit boards 34 may be attached to frame 12 in desired fashion, such as using conventional standoffs and appropriate fasteners.

Figure 3:
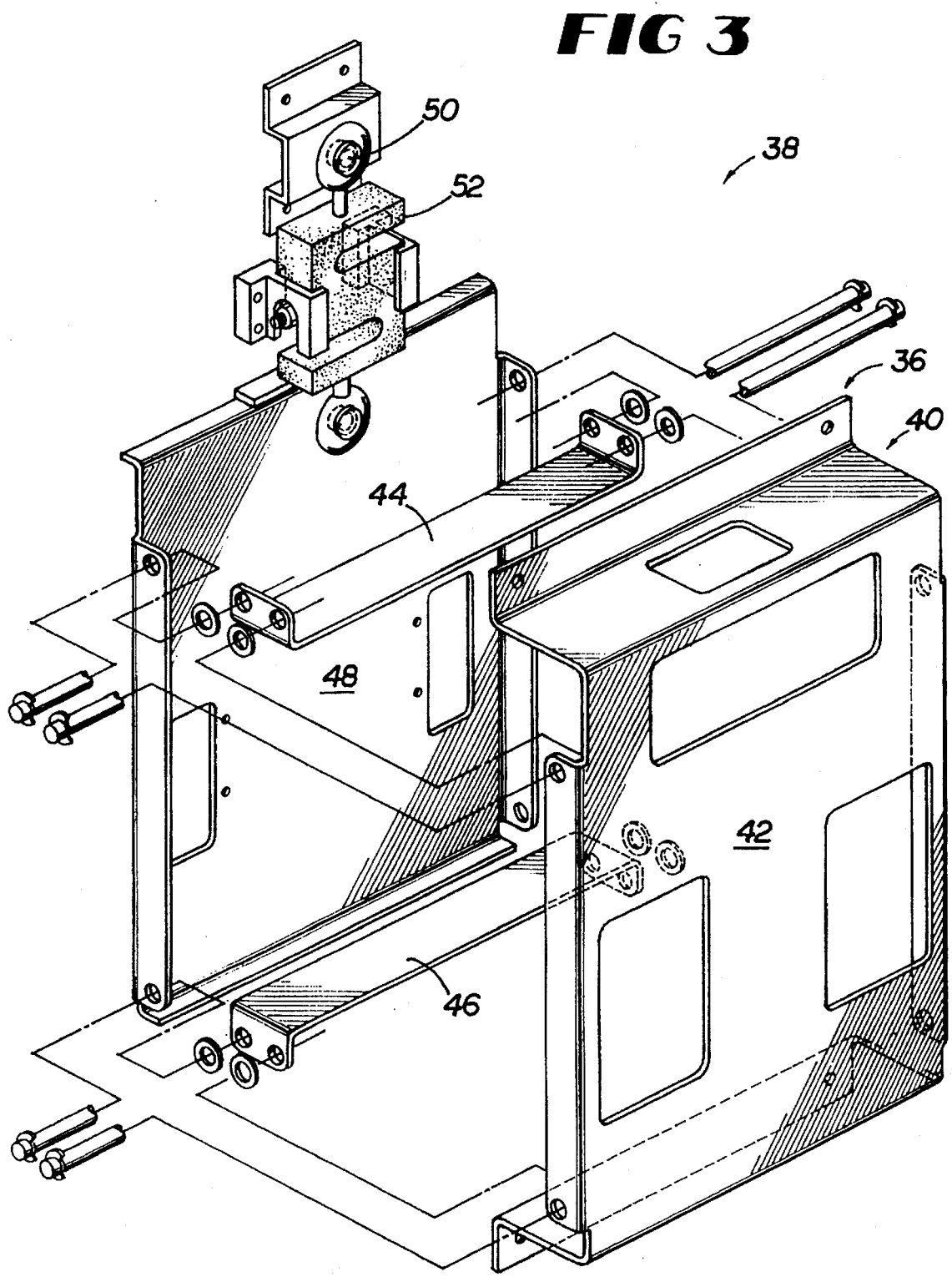
FIG. 3 is a perspective, exploded view of a load cell structure of the embodiment of the device shown in FIG. 1.

The rigid frame structure 30 for supporting container 32 is attached to frame 12 via a weighing mechanism that substantially zeroes out any bending moments and/or non-vertical force components imposed by container 32. Preferably this is a load cell 36. The load cell 36 is shown in FIG. 2 and more clearly in FIG. 3. The load cell 36 aims to allow frame structure 30 to suspend nonrigid container 32 without imposing any bending moments or nonvertical force components on the weighing components of device 10, so that all of the weight of articles and the container 32 is accurately measured by the weighing portion 38.

Load cell 36 preferably comprises a parallelogram-like structure 40 (generally in the shape and configuration of a parallelogram, when viewed in cross section) for accomplishing this purpose. A front vertical member 42 is attached via appropriate fasteners to frame 12 as shown in FIG. 2. Upper horizontal member 44 and lower horizontal member 46 are attached, preferably in hinged fashion, to front vertical member 42 and also to back vertical member 48 to form the parallelogram. Back vertical member 48 is in turn connected via a pin structure 50 to weighing structure 52 which is also attached at its upper end via a pin structure to frame 12. Weighing structure 52 may be attached to back vertical member 48 and frame 12 as otherwise desired, and may be formed in any appropriate conventional fashion.

In the preferred embodiment, weighing structure 52 is substantially S-shaped and carries at least one strain gauge for electrical sensing of deformation of weighing structure 52. Output of the strain gauge is connected to the microcontroller components 86 of the preferred embodiment for processing by those hardware and software components as discussed below. The slight deformation of the parallelogram-like structure 40 imposed by loads in container 32 are sufficiently small that non-vertical force components and bending moments imposed by loads in container 32 are negligible. Accordingly, weighing structure 52 senses, for all practical purposes, all of the load imposed by the contents of container 32.

The frame structure 30 supporting container 32 is also attached to back vertical member 48 of load cell 36, so that upper and lower horizontal members 44 and 46 constrain that structure 30 from rotating or translation in any but a substantially vertical direction (for all practical purposes, and ignoring floor and device misalignment and engineering tolerances, a vertical direction). In that vein, load cell 36 is sufficiently wide to provide a robust parallelogram-like structure that is intended to withstand cycles of abuse in the surgical suite, together with random impacts and lateral and vertical forces [bearing in mind that some users may (contrary to instructions) employ frame structure 30 to move or reposition the device 10].

The rigid frame structure 30 for supporting container 32 contains a rigid support frame 54 which may be formed of metallic and/or plastomeric material and configured to hold container 32 snugly but allow for easy deployment and removal of container 32. In the preferred embodiment, it is a metal web 56 finished out by a plastomeric flashing 57 that receives upper portions of container 32.

The rigid support frame 54 contains a plurality of sensors for sensing passage of articles into container 32. The sensors are preferably photodiodes or phototransistors which may operate in bursts (or continuously) as discussed more fully below. The sensors are connected to input/output components of the hardware and software components of the preferred embodiment as discussed more fully below. The sensors 58 may be situated and oriented as desired in support frame 54, such as on circuit boards mounted on web 56 or as otherwise desired. They are oriented to send and receive energy through upper portions of container 32 so that passage of an article into container 32 interrupts the energy and accordingly registers with device 10 for tracking.

Container 32 comprises a lower, receptacle portion 60 connected to an upper top member 62. Receptacle portion 60 may be formed in any rigid or nonrigid manner, but is preferably formed of thin but relatively impenetrable plastic, substantially clear, material having four sidewalls 64 and a bottom 66. The walls 64 are preferably tapered inwardly toward the bottom to allow easier insertion or removal of the container 32 into or from the frame 30 retention of device 10. One or more defining members 68 such as a corrugated or plastic insert of suitable shape, may be formed in lower portions of receptacle 60 and/or each retention portion 70 to be in or fall into place during deployment and lend shape, conformity, and definition to receptacle 60 for easier insertion of sponges or other articles. Receptacle 60 preferably, but need not, contain two or more retention portions 70, each for retaining a separate type or size of sponge or other article. Likewise, receptacle 60 may contain a single retention portion 70, when sorting of the articles is not required, such as occurs when articles contain identity markers that preclude sorting. In any event, visual inspection is made easier because each size of sponge is contained in its own portion of receptacle 60.

In the preferred embodiment, retention portions 70 are formed by inclusion of an interior wall 72 in any desired shape and configuration. Retention portions 70 preferably correspond to ports 74 that are formed in top member sorting grid of the receptacle 62. Each port is adapted to receive a separate type or size of sponge or article.

Port or ports 74 in sorting grid top member 62 preferably contain flashing 76 for guiding the articles into retention portions 70. Sorting grid top member 62, which is substantially rigid, may be formed of desirable plastomeric or other materials and conform in shape to cooperate with retention grid 54 of device 10 for a snug, but easily deployable and removable fit. Top member 62 preferably receives a cover or lid 78 which may be closed to form a closure or seal. Cover 78 may offer indicia 80 to indicate which type of articles correspond to each port 74. In the preferred embodiment, for instance, the left or first port 74 is for 4×4 inch sponges as shown in FIG. 1, while the right or second port is for lap-type (laparotomy) sponges. A third port 74 (and more ports if desired) may be included, together with a corresponding retention portion 70 and receptacle 60, for other types of sponges or articles such as neuropledgets used during neurologic surgery. In situations where identity markers or other article identification means or mechanisms are used, only one port need be included.

Container 32 contains at least one region 82 which is at least partially transmissive to energy emitted by sensors 58, in order to allow sensors 58 to sense passage of articles into container 32. In the preferred embodiment, since the walls 64 of receptacle 60 are substantially clear or transparent, sensor regions 82 are simply upper portions of receptacle 60 which are adjacent to sensors 58 when container 32 is mounted in frame structure 30 of device 10. In some cases, however, it may be desirable to have a container 32 with substantially translucent or opaque portions; in that event, regions 82 are windows formed of clear or substantially transparent material.

Container 60 may also contain an access port formed in sidewalls 64 of receptacle 60 for accessing sponges or other articles after they have been placed in container 32. Access port 84 is preferably adapted to be resealed in fluid-tight fashion. Access port 84 is useful in selected situations, such as when the anesthesia staff or nurse have doubts about sponge counts and wish to recount the sponges in order to ensure that no sponges have been left in a patient.

Container 32 is accordingly adapted to be manufactured inexpensively, and folded into a compact configuration for efficient shipping and handling. Nevertheless, device 10 is configured in a fashion that allows container 32 to be suspended, yet its contents accurately counted and weighed according to the present invention.

Container sensor 59 is adapted to sense presence or absence of container 32 on device 10. In the preferred embodiment, sensor 59 is a photodiode mounted on frame 12 and oriented to "see" either frame structure 30 (relevant portions of which are preferably colored dark) or container 32 (of a lighter color) when it is installed. Phototransistors, contact switches or other appropriate sensing devices may just as easily be employed as sensor 59.

Marker sensors 61 may also be employed with device 10 according to the present invention. These may be conventional scanners which are adapted to sense the presence of conventional IC transponders on or within articles in order to provide desired information about the articles or classes of articles in which they belong, including type, structure, size, composition (cotton, synthetic or other), manufacturer, date of manufacture, and other desired information. Similarly, the sensors 61 may be devices that establish electromagnetic fields and sense the presence of a conducting element in the fields, such as dipole wire elements, microchips, microtransponders, microtransmitters, or threads in the articles (which may be encoded if desired). They may similarly be radiation detectors adapted to sense radioactive tracers in the articles; receivers adapted to sense signals from transmitters in the articles; sensors adapted to sense radiopaque handles or threads in the articles; photoelectric sensors adapted to read bar or other codes in or on the articles; MRI detectors which sense MRI active polymers or other materials; color sensors, video sensors, capacitative sensors; transponders adapted to sense presence of passive electronic ID radio tags or other desirable means for identifying and/or counting individual articles or sponges. Marker sensors 61 are coupled to microcontroller components 86 in conventional fashion, and employing conventional code that takes advantage of the information provided by sensors 61 to display, store and/or output relevant to identification, counting and/or weighing of articles and/or their contents.

FIG. 4 is a block diagram of hardware components of a preferred embodiment of the present invention. Microcontroller components 86 are coupled to user panel, display and switch interface 88, sensor components 90 (which are connected to sensors 58, container presence sensors 59, identity or marker sensors 61), and load cell 36. They may also be interfaced with marker sensors 61 as discussed above.

Microcontroller components 86 sample data provided by display and switch interface 88, sensor components 90, article sensors 58, container presence sensors 59, marker sensors 61, load cell 36 and configuration port 92 in order, among other things, to sample user commands, sensor 58 status for passage of articles, load cell 36 for weight of contents, container presence sensors 59 for presence of containers 32, and marker sensors 61 for signals from markers in articles. The device uses this information to calculate, display and provide, among other things, net weight (and thus volume) of the contents and count of the articles contained in container 32. Configuration port 92 allows new software to be loaded, reconfiguration to occur, and connection of device 10 to network or other telecommunication means. The microcontroller components 86 accomplish these tasks according to the software processes shown in FIGS. 5-16.

In the interpretation of FIGS. 5-16 which contemplate a preferred embodiment of the invention:

(1) A block represents an "External" which is something outside the software system, usually a hardware module.

(2) Continuous data flow is represented by a solid, double-arrowed line. A continuous data flow is a constant supply of data which is not a response to an event or input.

(3) Software processes are indicated by solid circles, and are any processes that perform an operation on data coming in, or generate data going out.

(4) An event flow is represented by an interrupted arrowed line. It typically contains a minor amount of data, sufficient only to identify the event.

(5) A control process is indicated by an interrupted circle. Control processes typically have as their subjects either a piece of hardware or events generated from time).

(6) Data flows are represented by solid, single-arrowed lines. They may originate from processes, Externals, data stores or control processes. They may also arrive at any of these.

(7) Data stores are represented by parallel horizontal lines. They hold information at rest, usually in memory.

Figure 4A:
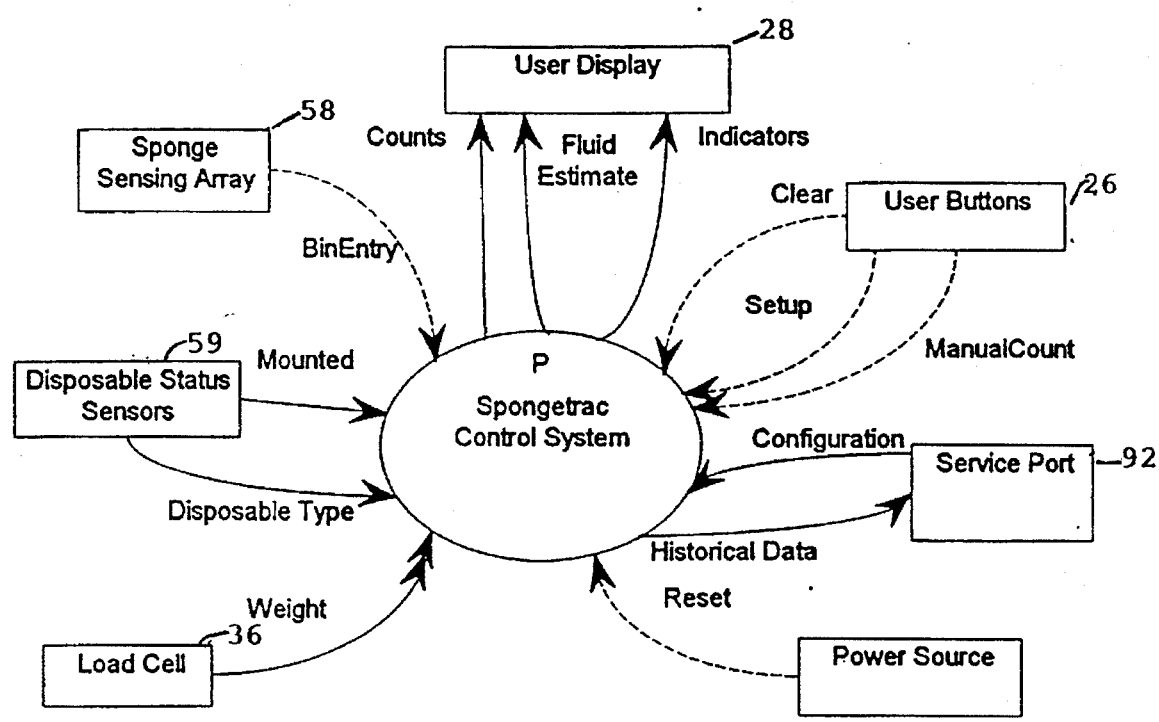
FIG. 4A is a context diagram which shows the relationship of software of the preferred embodiment with its environment.

FIG. 4A is a context diagram which shows the relationship of software of the preferred embodiment with its environment. The Externals correspond to elements described above, including user buttons 26, indicators or display 28, sensors 58, load cell 36, and container presence sensors 59. The software also communicates with configuration port 92 and a power source for reset.

In essence, software according to the preferred embodiment is adapted to respond to a number of events, including: (1) device 10 is powered and a reset occurs; (2) the user presses the clear button; (3) the user presses any manual count (decrement or increment) button; (4) the user presses any of the setup buttons; (5) a disposable is mounted on the unit; (6) a disposable is removed from the unit; (7) an object enters any of the ports; (8) a sensor on any of the ports becomes blocked; (9) the weight of the container or its contents changes; (10) the user enters a command at the service port; or (11) display time for updating display data. Additional events include the device recognizing a marker in an article.

According to a preferred embodiment of the present invention, the microcontroller is an MC68332 which is designed for embedded control applications. This IC contains a central processing unit, a time processing unit, memory and several types of interface circuits. Any suitable digital signal processor as desired may be used as microcontroller 86. Numeric displays are preferably formed of multiple seven segment LEDs. Discrete LEDs are preferred as indicators of operator actions. The software sees all of these elements in a single serial output string. The Queued Serial Peripheral Interface within the microcontroller unit is employed to output this data.

Any button 26 pressed on the user panel 24 will invoke and interrupt of the CPU. The software interrogates specific memory addresses to identify the user button 26. The interface provides up to 16 buttons of which 11 may be used. The service port is a standard serial interface which connects with a terminal, PC or telecommunications means.

As discussed above, the load cell 36 is adapted to indicate the load or weight of the container 32 and its contents by providing a voltage to an analog-to-digital converter. The converter in turn provides a 12-bit number to the software which represents the weight. Disposable or container 32 sensors 59 indicate an on or off state.

The sensors 58, in the preferred embodiment photodiode arrays, preferably involve a carrier output from the time processor unit and a return carrier from each port into the time processor unit. The software examines each return carrier to determine if an event has occurred at any port. The event may be either a sponge entering the port or blockage of sensors 58 for that port.

Control of device 10 via user panel 24 and buttons 26 (shown in FIGS. 1A and 1B) occurs preferably in the preferred embodiment as follows. Each of buttons 26 causes specific things to happen. In addition, each button may be armed and disarmed under specific conditions. All buttons are preferably disarmed, for instance, during power up/self-test of the device 10. The function of each button is preferably as described below together with conditions under which it is armed and disarmed.

A clear button is employed at the start of an operation or surgical procedure. The clear button sets each of the counts for each port 74 to "0000." Two or more counts may be employed depending on the type of container 32 in use. The clear button also sets the fluid display to "0." The clear button finally is employed to arm other buttons which may be used to set up device 10, including sponge-type buttons, such as for cotton, synthetic, vaginal or mini sponges.

The clear button is armed when the container 32 is not mounted on support frame 54. It becomes disarmed when a container is so mounted and one count is registered in any port 74. The count may originate from a sponge passage or by an increment or decrement button. Increment and decrement buttons are provided, preferably corresponding to each port 74, for those times when a count must be manually adjusted by the user. These buttons are armed when the container 32 is mounted on support frame 54 of device 10 and disarmed when dismounted.

COTTON and SYNTH buttons indicate the type of material from which sponges are made. The COTTON button selects cotton and SYNTH selects synthetic material. When either button is pressed, the respective display for cotton or synthetic is illuminated to indicate the selection that has been made. This selection is important, because different dry weights are stored for different material types in order to tare the weight of sponges. Default is cotton. The COTTON and SYNTH buttons are armed by the clear button, but are disarmed when the container 32 is mounted and one count has been registered.

Sponge size buttons, such as VAG LAP (gynecologic) and MINI LAP (mini-laparotomy) sponges, are employed to select alternate sizes for the ports. The left port may, for instance, have a MINI LAP button attached to its count display, while the right port may have both VAG LAP and MINI LAP buttons. A regular size lap sponge is selected by default for the right port 74, and a 4×4 is selected for the left upon power up. Pressing either VAG LAP or MINI LAP will select that sponge size. Pressing that button again will deselect that type and reselect the default sponge. If MINI LAP is selected as either port and the operator selects MINI LAP at the other port, then the port previously selected for MINI LAP sponges will reset to default. Again, the primary significance is due to the employment of different dry weights to tare the sponge weights during the weighing process. The VAG LAP and MINI LAP buttons are armed by the clear button and disarmed when a container 32 is mounted in one count register.

User outputs according to the preferred embodiment preferably include a first five-digit fluid display, and a second three-digit display for each port and several discreet displays, together with an audible output. The fluid display shows fluid in milliliters and is updated preferably within one second of the time sponge entry is detected at any port. The count display for each port shows the number of sponges detected to have entered the port as corrected by the increment/decrement buttons for that port. For instance, if a sponge enters the incorrect port, the increment/decrement buttons may be employed to correct the count rather than the user being required to extract a sponge from the unit and place it in the correct port. Counts are preferably updated within 1/10 second from sponge detection. Manual count LEDs indicate manual count for each port. These indicators are off until a manual count button has been pressed. The fluid display, count display and manual count display are illuminated until the clear function has been executed. Discrete displays such as LEDs, indicate selection of cotton or synthetic sponges and VAG LAP or MINI LAP sponges instead of default sponges.

The audible output alerts the user when sponge counts for any port have reached a warning level. One or more warning levels may be employed, such as one at a count of 20, and another at a count of 30 sponges.

The following disclosure, as does the disclosure above, relates to a preferred embodiment of the present invention. Accordingly, dictionary and data definitions, identity of data or data objects which are captured, stored and displayed, data fields and formats, data flow, steps, sequences, display and reporting formats, electronic components, other components, and other aspects of apparatus and processes according to the present invention may be accomplished differently in order to function substantially the same way and to achieve substantially the same result as the present invention.

Figure 5:
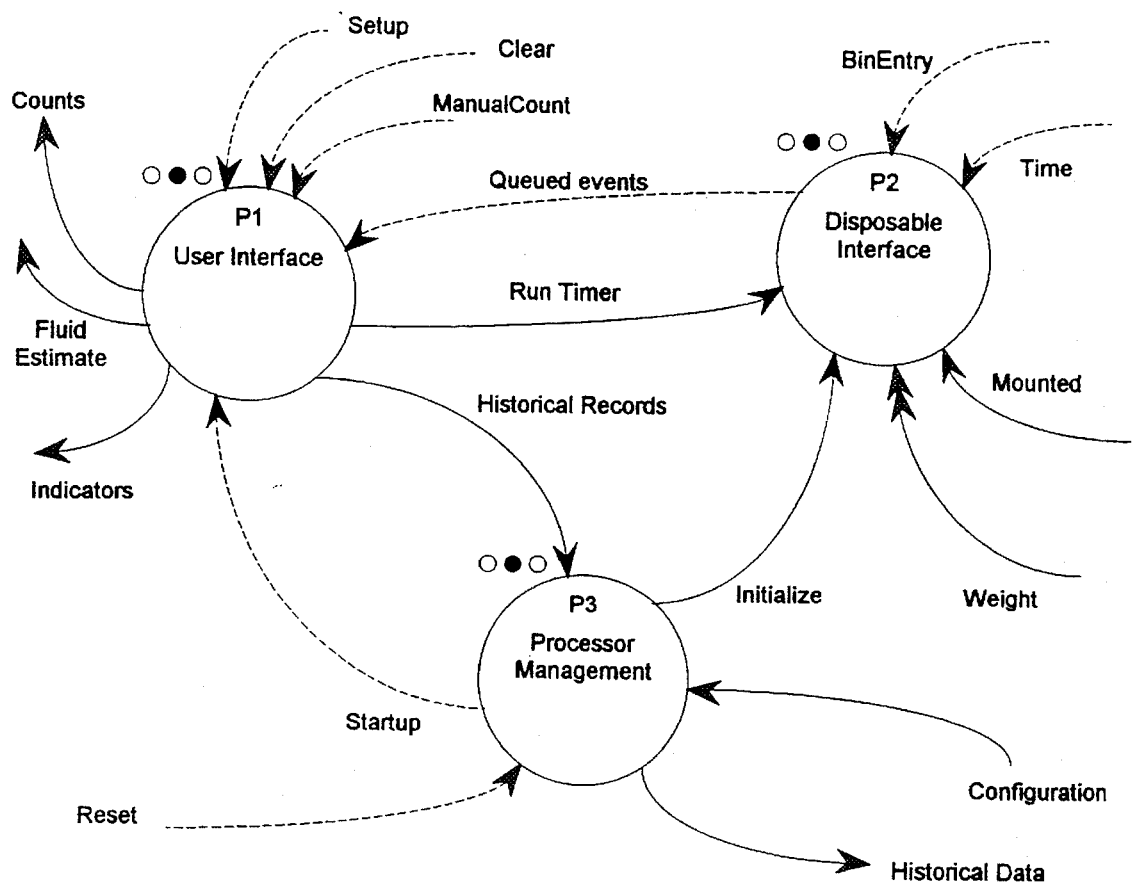
FIG. 5 is a top level diagram of software processes according to a preferred embodiment of the present invention.
Figure 6:
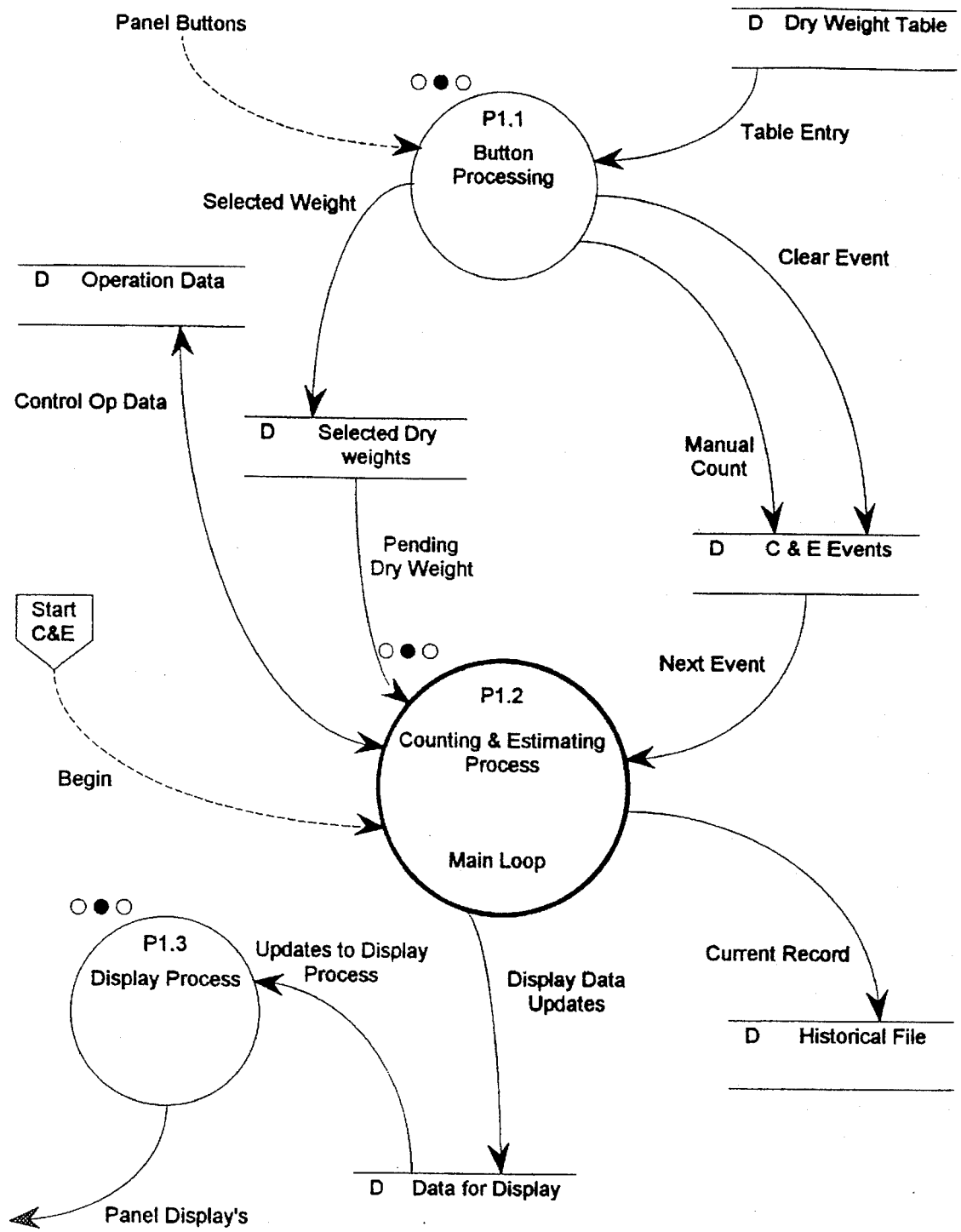
FIG. 6 is a user interface data flow diagram according to a preferred embodiment of the present invention.
Figure 7:
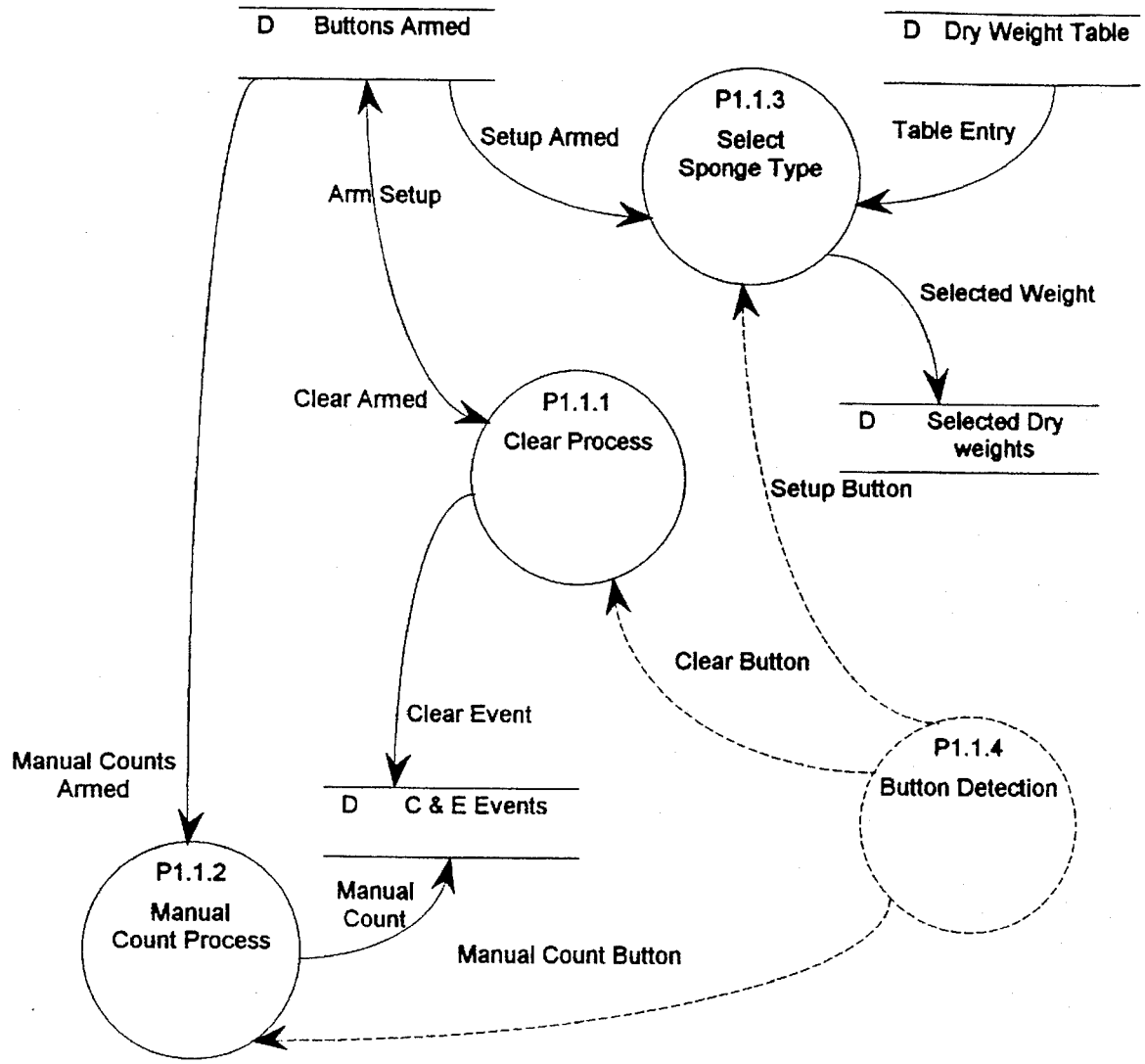
FIG. 7 is a button processing data flow diagram according to a preferred embodiment of the present invention.
Figure 8:
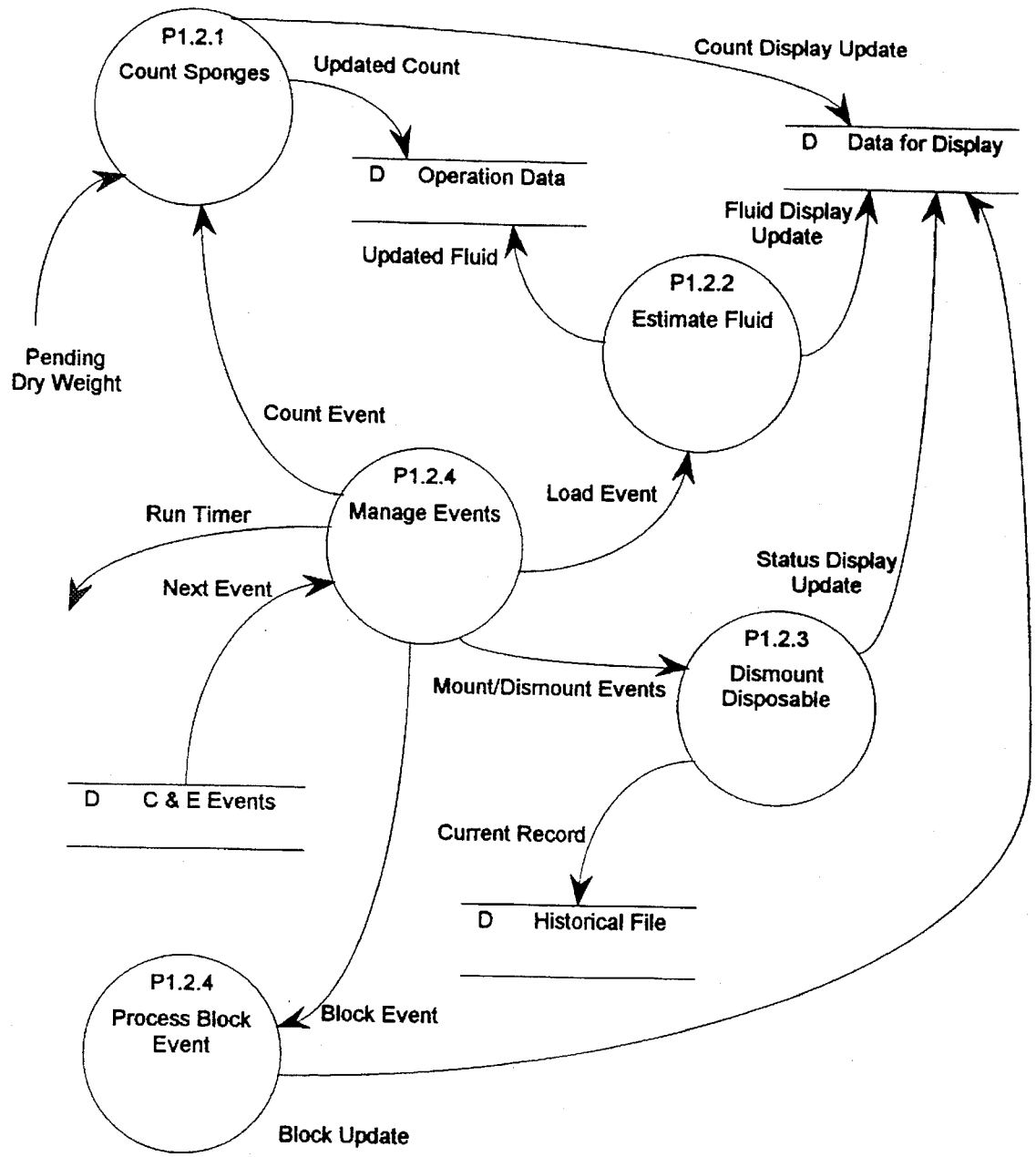
FIG. 8 is a counting and estimating data flow diagram according to a preferred embodiment of the present invention.
Figure 9:
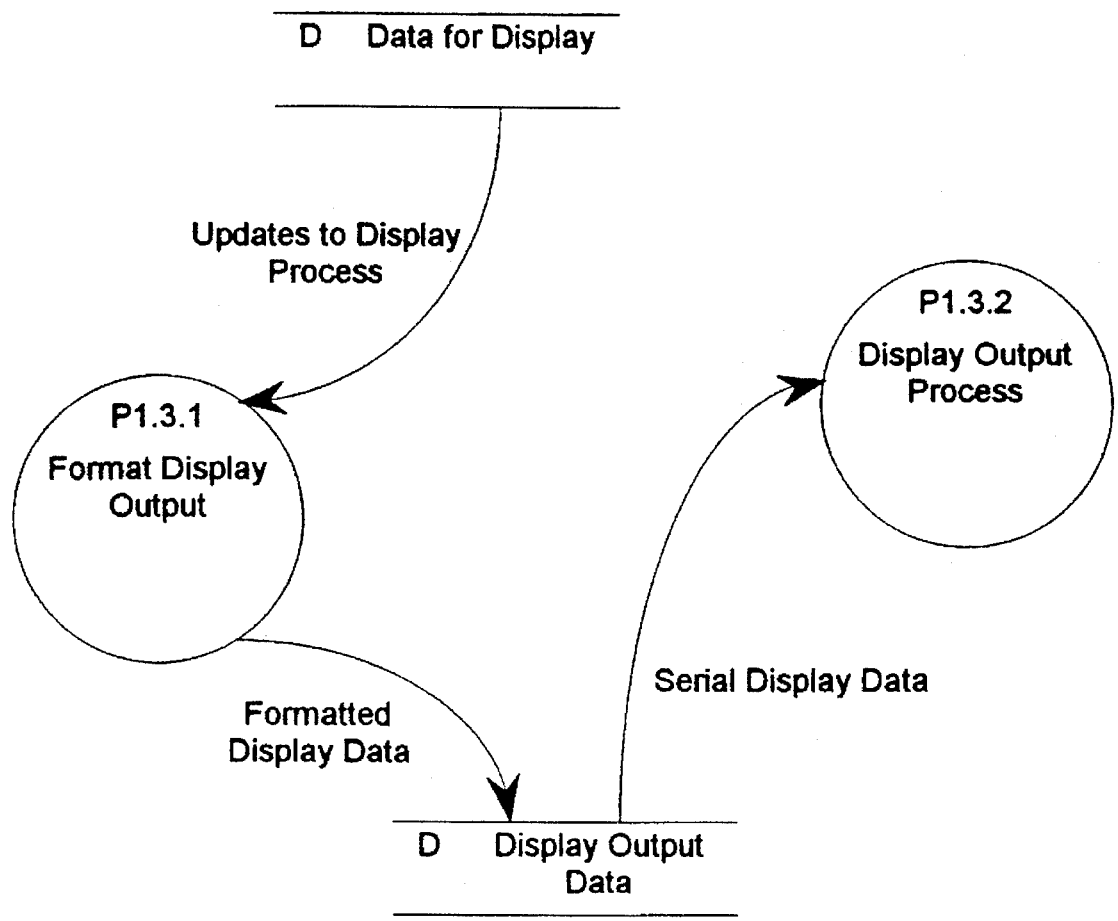
FIG. 9 is a display process data flow diagram according to a preferred embodiment of the present invention.
Figure 10:
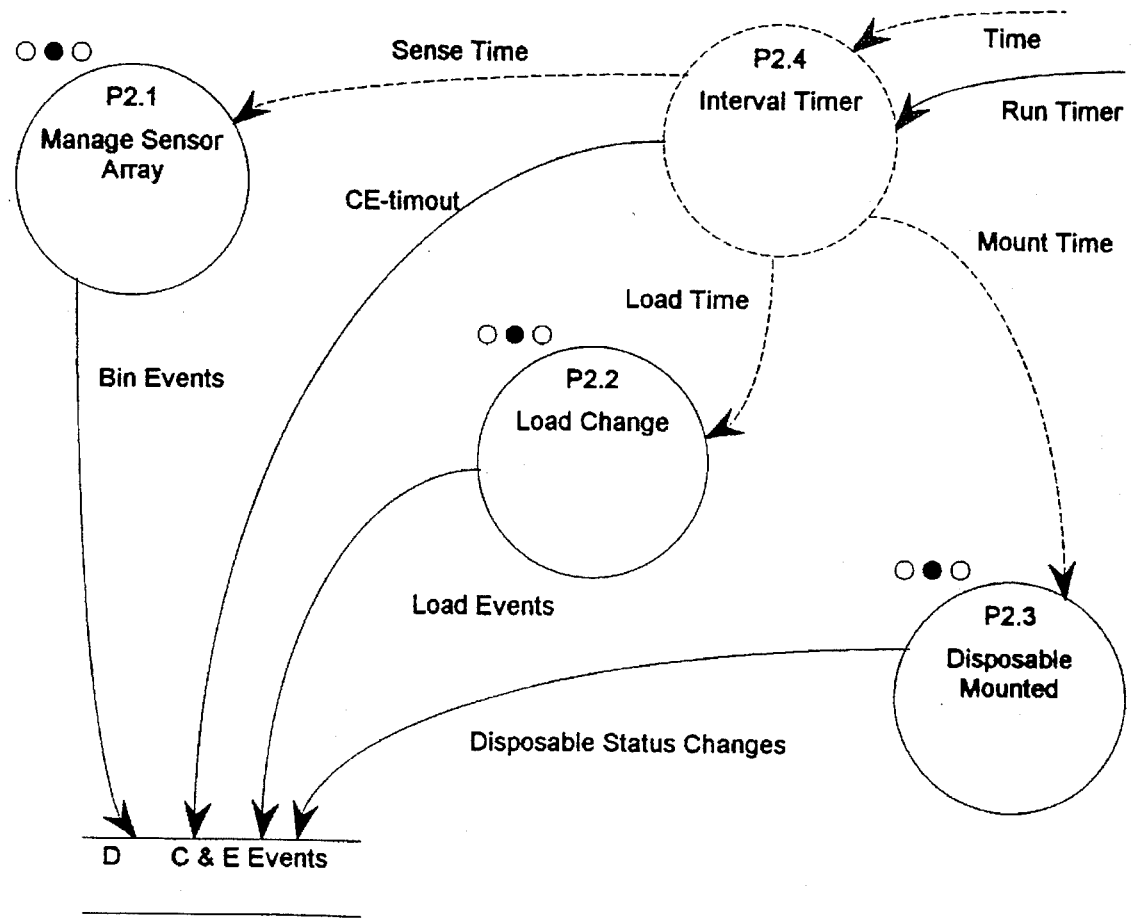
FIG. 10 is a disposable interface data flow diagram according to a preferred embodiment of the present invention.
Figure 11:
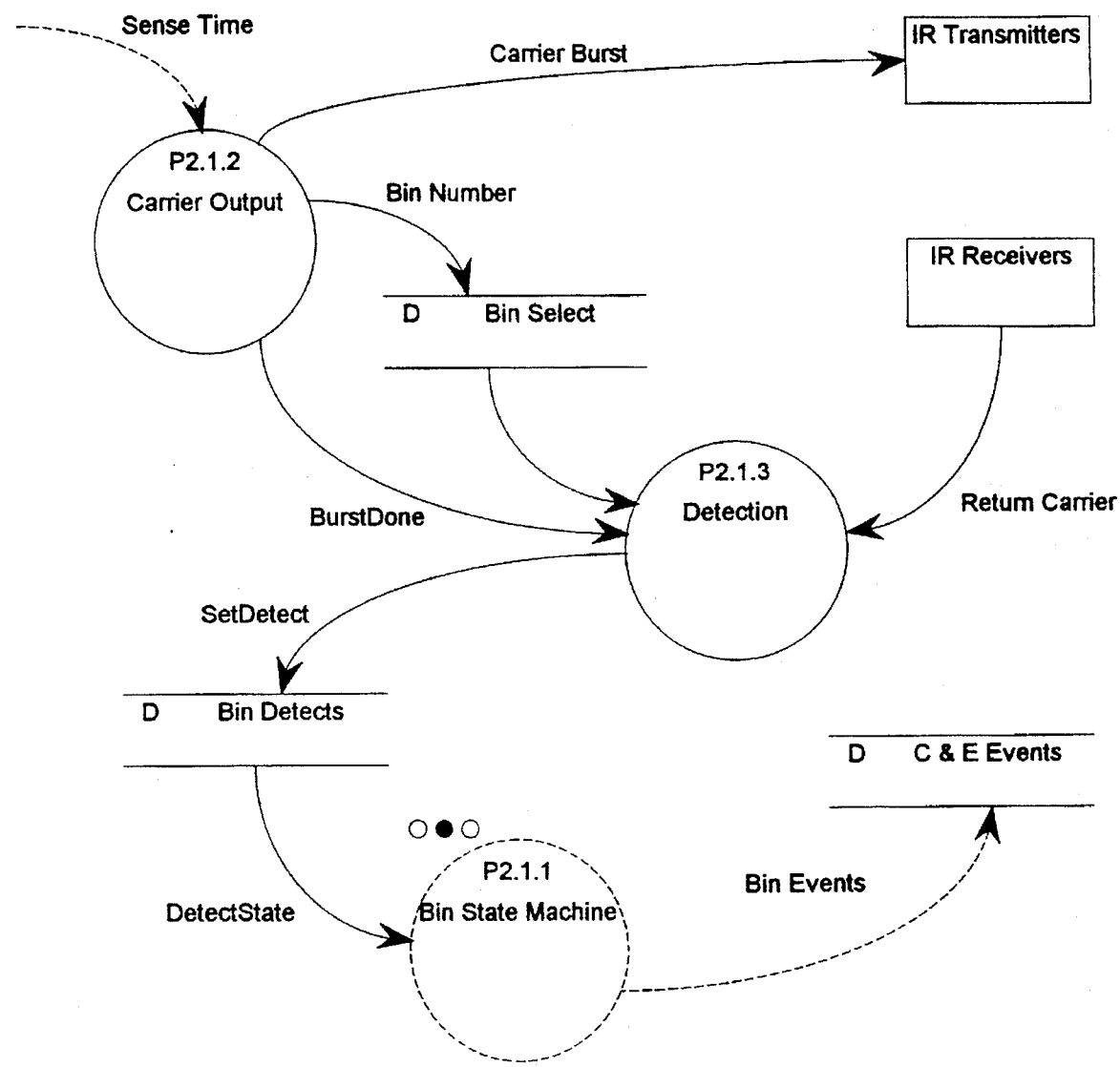
FIG. 11 is a sensor array data flow diagram according to a preferred embodiment of the present invention.
Figure 12:
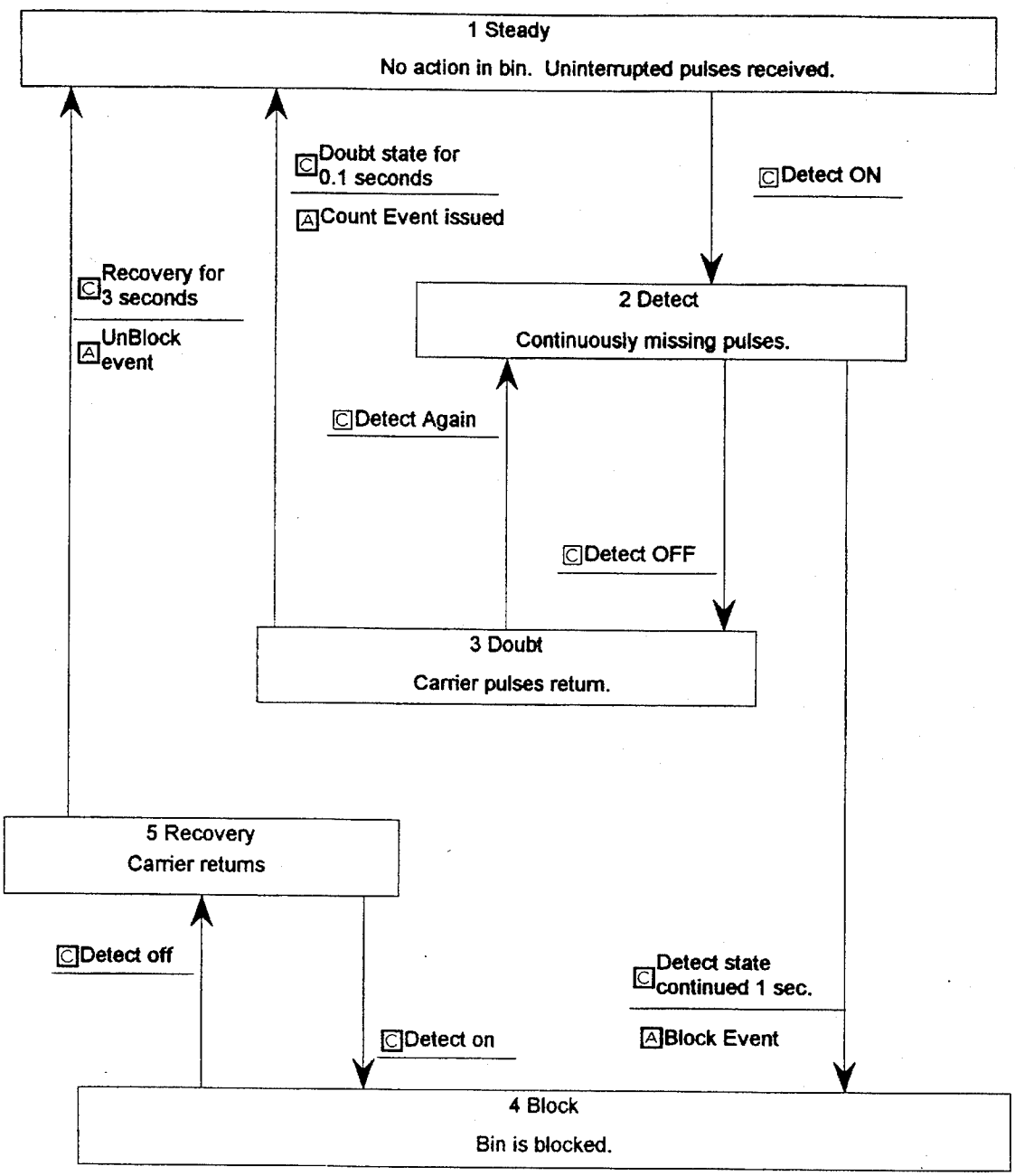
FIG. 12 is a sensor logic diagram according to a preferred embodiment of the present invention.
Figure 13:
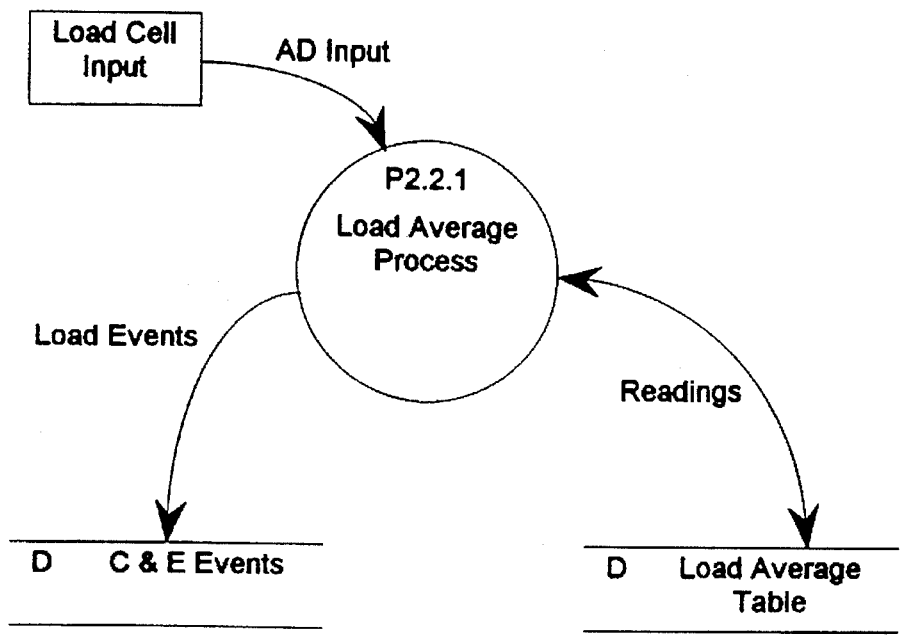
FIG. 13 is a load averaging data flow diagram according to a preferred embodiment of the present invention.
Figure 14:
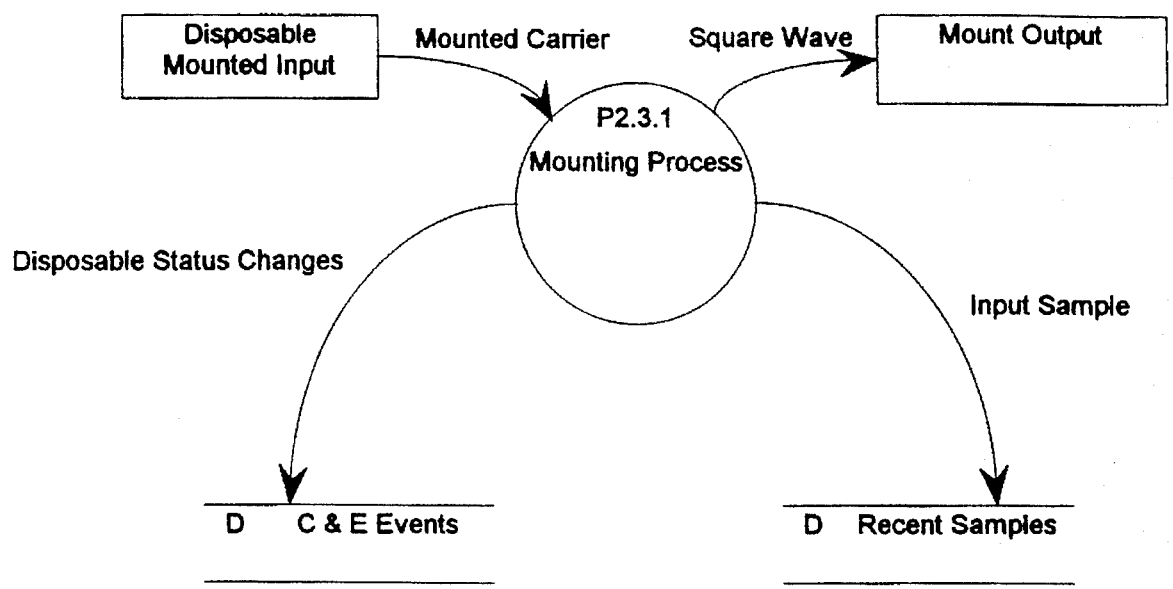
FIG. 14 is a mounting process data flow diagram according to a preferred embodiment of the present invention.
Figure 15:
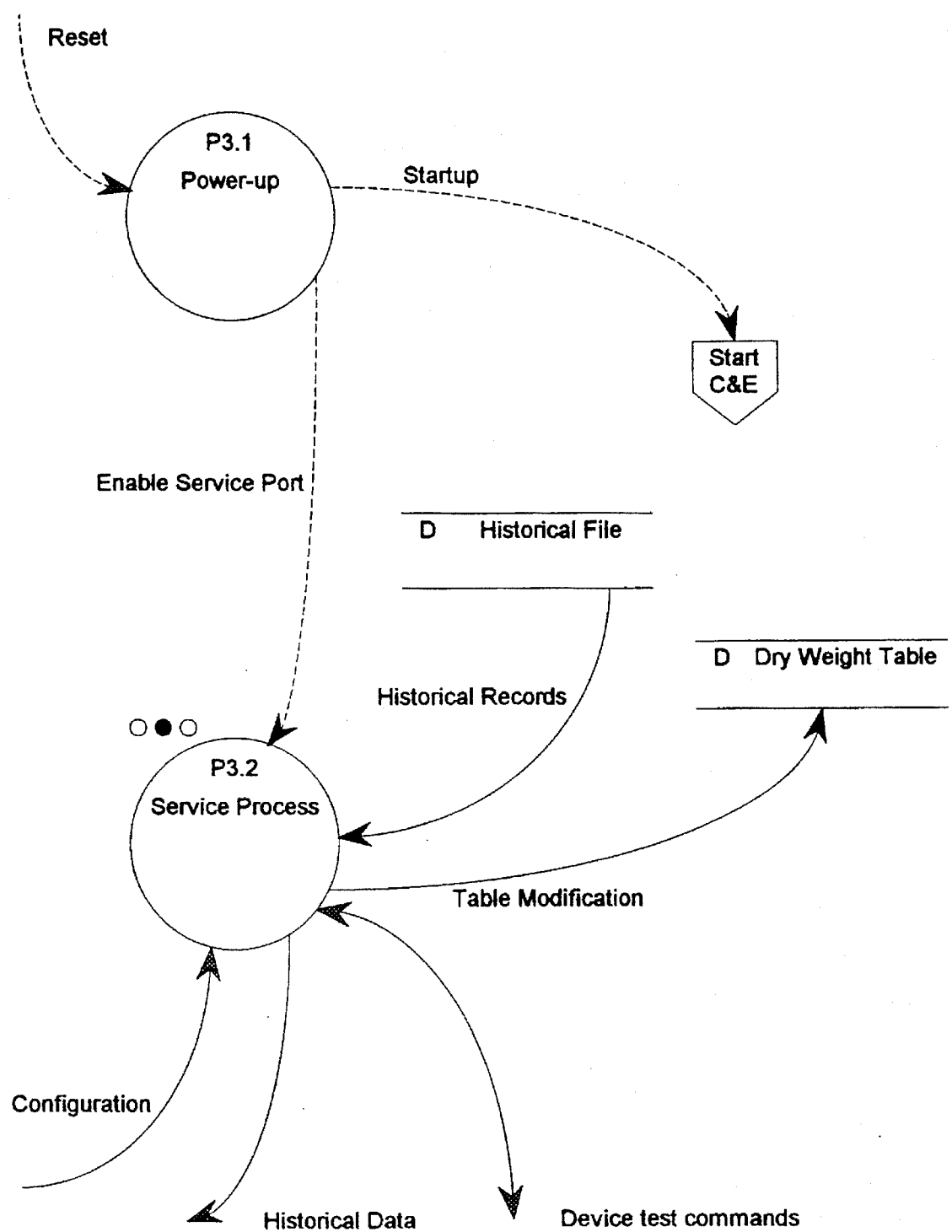
FIG. 15 is a processor management data flow diagram according to a preferred embodiment of the present invention.
Figure 16:
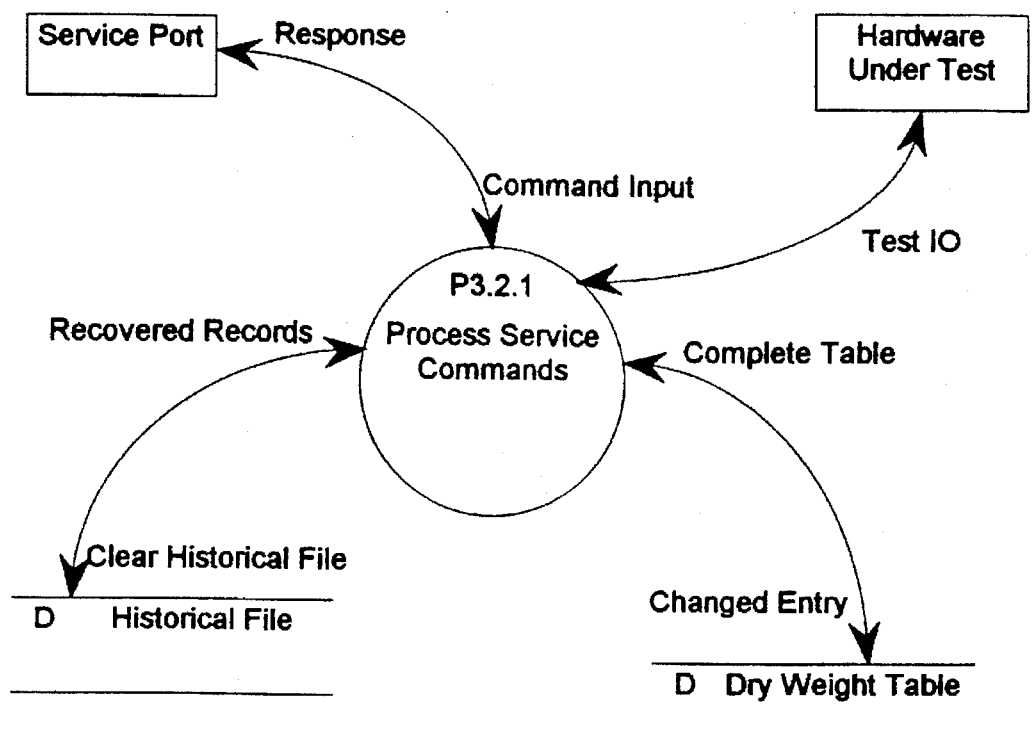
FIG. 16 is a service process data flow diagram according to a preferred embodiment of the present invention.

Subject to the foregoing, FIG. 5 is a top level data flow diagram which shows relationship of user interface, disposable interface and processor management processes. FIGS. 6–9 show subprocesses of the user interface process. FIGS. 10–14 show subprocesses of the disposable interface process, and FIG. 15 shows processor management process.

For purposes of the following discussion, software according to the present invention uses the following data dictionary. The term "bin" means the same as retention portion 70, and "disposable" is used interchangeably with container 32.

| Data Dictionary | | |
|---|---|---|
| Name | Type | Description |
| AD Input | Data Flow | *Data from Analog to Digital Converter* |
| ADCinput | Data Element | *Reading from Analog to Digital Converter; twelve bits* |
| BagCount | Data Element | *Sponge Count for a bin in one disposable* |
| Begin | Data Flow | *Start Counting & Estimating ("C&E" or "CE")* |
| Bin Events | Data Flow | CE-event |
| BinDetect | Data Flow | *Sensors detect entry into a bin* |
| BinEntry | Data Flow | *Bin entry Event* |
| BinNumber | Data Element | *Disposable bin number left to right 1,2 and 3* |
| Block | Data Element | *On to indicate the bin is blocked* |
| Block Event | Data Flow | CE-event |
| Block Update | Data Flow | *Update blocked bin status* |
| Button Detection | Process | *Detects buttons pressed* |
| Button Processing | Process | ** |
| Buttons Armed | Data Store | @ClearArmed +SetupArmed +ManualCountsArmed |
| C & E Events | Data Store | CE-event |
| CE-event | Data Structure | @TypeEvent +BinNumber |
| Carrier Setup | Data Flow | *Carrier to transmitters* |
| Clear | Data Flow | ** |
| Clear Armed | Data Flow | ** |
| Clear Button | Data Flow | ** |
| Clear Data | Data Flow | ** |
| Clear Process | Process | *Makes device ready for new operation* |
| Clear-Armed | Data Element | *Arm the clear button* |
| Command Input | Data Flow | *Operator enters command and system responds* |
| Complete Table | Data Flow | ** |
| Configuration | Data Flow | *Modified table entry* |
| Configure Sponge Weights | Data Flow | DryWeight |
| Control Op Data | Data Flow | *Operation data is controlled by the Counting & Estimating Process* |
| Cotton-LED | Data Element | *Turn on the COTTON indication* |
| Count Display Update | Data Flow | *Updates count and warning flag for bin* |
| Count Event | Data Flow | CE-event |
| Count Sponges | Process | *Process a sponge count* |
| Count Wait Timer | Process | *Started by load event under blocked bin conditions* |
| Count Wait Timeout | Data Flow | ** |
| Count1Left | Data Element | *Accumulated sponge count for the left bin* |
| Count2-Center | Data Element | *Accumulated count for the center bin* |
| Count3- | Data | *Accumulated count for the right bin* |

Data Dictionary

| Name | Type | Description |
|---|---|---|
| Right Counting & Estimating Process | Element Process | *The main loop of the system* |
| Counts | Data Flow | *Counts are updated on display* |
| Current Record | Data Flow | @DeviceRecord |
| Current-Count | Data Element | *The current count for display* |
| Data for Display | Data Store | @DisplayFluid + ErrorFlag +1{DisplayCount}3 +CottonLED +SynthLED +VagLED +MiniLED |
| Detection | Data Element | *Detection flag* |
| Device-Record | Data Structure | @SequenceNumber +DispoType +1{SpongeType}3 +1{BagCount}3 +EstimatedFluid |
| Discount Disposable | Process | *Process mount and dismount events* |
| Display-Data Updates | Data Flow | ** |
| Display Output Data | Data Store | *Serial data stream* |
| Display Output Process | Process | *Queued serial output process* |
| Display-Count | Data Structure | @CurrentCount +ManualCount +Block +Warning |
| Display-Fluid | Data Element | *Estimated sponge fluid for display* |
| DispoType | Data Flow | *Type of disposable mounted* |
| DispoType | Data Element | *Type of disposable in use, two or three hole* |
| Disposable Interface | Process | *Collect Disposable Interface data and send events to C & E Process* |
| Disposable Mounted | Process | *Monitor disposable status* |
| Disposable Mounted Input | External | *Discrete input, either On or Off* |
| Disposable Status | Data Flow | *Status of disposable* |
| Disposable Status Changes | Data Flow | CE-event |
| Disposable Status Sensors | External | |
| Disposable Type | Data Flow | *Two or Three hole* |
| Disposable-Status Sensors | External | *Sense disposable type and mounted* |
| Dry Weight Table | Data Store | 1{DryWeight}18 |
| DryWeight | Data Element | *Weight of a dry sponge in grams* |
| Enable Service Port | Data Flow | ** |
| ErrorFlag | Data Element | *Tells Display process to show Error on fluid display* |
| Est-Fluid | Data Flow | *Updated fluid estimate* |
| Estimate Fluid | Process | *Estimate incremental fluid* |
| Estimated-Fluid | Data Element | *Accumulated fluid estimate for operation. Includes current and previous disposables* |
| Fluid Display Update | Data Flow | ** |
| Fluid Estimate | Data Flow | ** |
| Fluid Estimate | Data Flow | *Numeric data for fluid display* |
| Format Display Output | Process | *Produce serial data stream for display output hardware* |
| Formatted Display Data | Data Flow | *Display data formatted for QSPI output to the display driver chips* |
| Historical Data | Data Flow | *Record on each disposable used* |
| Historical File | Data Store | 1{DeviceLRecord}1000 |
| Historical Records | Data Flow | *Device history records* |
| Indicators | Data Flow | *LED's for manual counts and setup* |
| Input Sample | Data Flow | *Save sampled state* |
| Load Average-Table | Data Store | 1{ADCinput}16 |
| Load Cell | External | *Provides signal representing weight of disposable* |
| Load Cell Input | External | *Load cell connected to ADC* |
| Load Change | Process | *Sample load cell input for change* |
| Load Change Events | Data Flow | CE-event |
| Load Event | Data Flow | CE-event |
| Load Settling Timer | Process | *Started by count event to wait for load to settle* |
| Load Settling Timeout | Data Flow | ** |
| Load-Value | Data Flow | *Load cell data* |
| Manual Count | Data Flow | CE-event |
| Manual Count Button | Data Flow | ** |
| Manual Counts Armed | Data Flow | ** |
| Manual-Count | Data Flow | *Any of the six count buttons* |
| Manual-Count | Data Element | *Flag to indicate manual count(s) for bin* |
| Manual-Count Process | Process | *Creates a Manual Count Event* |
| Manual-Counts-Armed | Data Element | *Arm the manual count buttons* |
| MiniLED | Data Element | *Turn on the Mini Lap indication* |
| Mount/Dismount Events | Data Flow | CE-event |
| Mounted | Data Flow | *Indicates disposable in place* |

Data Dictionary

| Name | Type | Description |
|---|---|---|
| Mounted State | Data Flow | *ON or OFF* |
| Next Event | Data Flow | CE-event |
| OffCount | Data Element | *Number of samples a discrete input is Off* |
| OnCount | Data Element | *Number of samples a discrete input is On* |
| Operation Data | Data Store | @SequenceNumber +EstimatedFluid +Count1Left +Count2Center +Count3Right +SelectSponge1 +SelectSponge2 +SelectSponge3 +DispoType |
| Pending Dry Weight | Data Flow | DryWeight |
| Power Source | External | *Power supply, source of reset* |
| Power-up | Process | *Power up & Self test; start service process if CLEAR button pressed.* |
| Process Block Event | Process | ** |
| Processor Management | Process | *Reset/Startup/Selftest/Service* |
| Readings | Data Flow | *Readings from ADC for averaging* |
| Recent Samples | Data Store | @OnCount +OffCount |
| Recover Records | Data Flow | DeviceRecord |
| Recovered Records | Data Flow | ** |
| Reset | Data Flow | *Reset from a power up* |
| Return Carrier Timing | Data Flow | *Carrier received from multiple sensors* |
| Route C & E Events | Process | *Routes events and starts timers when necessary* |
| Select Sponge Type | Process | ** |
| Select-Sponge1 | Data Element | *Type of sponge selected for the left bin. This is the column number from the dry weight table* |
| Select-Sponge2 | Data Element | *Type of sponge selected for the center bin* |
| Select-Sponge3 | Data Element | |
| Selected Dry weights | Data Store | 1{DryWeight}3 |
| Selected Weight | Data Flow | DryWeight |
| Self Test OK | Data Flow | *Begin Counting & Estimating* |
| Sensor Array Input | Process | *Sponge sensing and blockage detection are done here* |
| Sensor Interface Process | Process | *Setup transmit carrier and check receive carrier for interruptions* |
| Sensor/Carrier Receivers | External | *IR receivers and circuitry* |
| Sensor/Carrier-Transmitter | External | *IR transmitters and circuitry* |
| Sequence-Number | Data Element | *Disposable number for operation, 1,2,3...* |
| Serial Display Data | Data Flow | ** |
| Serial Port | External | *Connected to dumb terminal or personal computer* |
| Service Port | External | *For sponge weight configuration and historical data output* |
| Setup | Data Flow | *Any setup button* |
| Setup Armed | Data Flow | ** |
| Setup Button | Data Flow | ** |
| Setup-Armed | Data Element | *Arm setup (sponge selection) buttons* |
| Sponge Detection | Data Flow | *Sponge detection events* |
| Sponge Sensing Array | External | *IR sensors for sensing bin entry* |
| Sponge-Sensing Array | External | *Senses sponges falling through grid holes* |
| Sponge-Type | Data Element | *Column number from Dry Weight Table* |
| Spongetrac Control System | Process | *The software as a whole* |
| Start C&E | Description | *Starts C & E after startup self test* |
| Start CWT | Data Flow | *Start the count wait timer* |
| Start LST | Data Flow | *Start load settling timer* |
| Startup | Data Flow | *Reset from power up* |
| Status Display Update | Data Flow | *Update disposable status* |
| SynthLED | Data Element | *Turn on the Synth indication* |
| Table Entry | Data Flow | DryWeight |
| TypeEvent | Data Element | *The type of event* |
| Updated Count | Data Flow | ** |
| Updated Fluid | Data Flow | ** |
| Updates to Display Process | Data Flow | ** |
| User Buttons | External | *For input of manual counts and sponge type* |
| User Display | External | *Numeric and discrete indicators* |
| User Display's | External | *Display sponge counts and estimated fluid* |
| User Interface | Process | *Process user inputs and display outputs* |
| VagLED | Data Element | *Turn on the Vag indication* |
| Warning | Data Element | *On to indicate a warning level; time to flash* |
| Weight | Data Flow | *Disposable weight* |

User Interface Module

FIGS. 6–9 relate to the User Interface Processes, which are responsible for presenting information to the user. Such information is received from other software processes and rendered into a user presentable form. Functionally, the User Interface Processes may be considered to engage in several subprocesses: (1) counting and estimating; (2) counting; (3)

estimating; (4) mode settling timeout; (5) count wait timeout; (6) disposable removed function; and (7) error function.

Counting and Estimating

The counting and estimating process may be considered as the main loop of software according to the preferred embodiment. The process waits for input or an event from other software processes, after having been entered when a container 32 is sensed as properly mounted on retention grid 54 and the device is operating properly. This may occur after power up/self test or the Disposable Removed process.

The User Interface Module is responsible for presenting information to the user. The information is received from other software modules and processed into a user presentable form. This module also contains the software drivers used to interface with the user panel 24 electronics. Steps occur as follows:

- Since the process begins with a new Disposable, the BAG COUNTS (counts of sponges or articles within container 32) are set to zero. PANEL COUNTS are not altered since they may have amounts carried over from previous Disposables.
- The User Interface panel is updated with the current PANEL COUNTS.
- The process waits for a COUNT EVENT, BLOCK EVENT, LOAD EVENT or a DISMOUNT EVENT from the Disposable Interface module; or, a TIME OUT EVENT from the LOAD SETTLING TIMER or the COUNT WAIT TIMER. This timer is used to give the load cell time to settle after a sponge has been detected.
- Upon receipt of a DISMOUNT EVENT the Disposable Removed process is initiated.
- Upon receipt of a BLOCK EVENT (relevant sensors 58 have been blocked) the applicable BIN BLOCK FLAG is set to ON. The count display for the blocked bin is set to alternate between "Err" and the bins PANEL COUNT. COUNT EVENTS for the blocked bin may occur but will originate from the user panel only.
- Upon receipt of an UNBLOCK EVENT the BIN BLOCK FLAG is cleared for the affected bin. The PANEL COUNT is restored to continuous display. Once again, COUNT EVENTS are allowed for the affected bin.
- Upon receipt of a COUNT EVENT the Count process is executed.
- Upon receipt of a LOAD EVENT the Fluid Estimate process is executed to determine if additional fluid has been deposited in the Disposable.
- Upon receipt of a TIME-OUT EVENT from the LOAD SETTLING TIMER, the Load Settling Time-out process is executed.
- Upon receipt of a TIME-OUT EVENT from the COUNT WAIT TIMER, the Count Wait Time-out process is executed.

Count Process

A valid COUNT EVENT has been received and must be processed by the software. The count must be registered on the appropriate user display, and a check must be performed to see if the Disposable is potentially filled to a point where it could block the sensor array. User warnings will be issued, preferably, when a count is equal to twenty or greater than or equal to thirty.

- First the PANEL COUNT and BAG COUNT for the appropriate bin are incremented.
- The user display is updated with the new PANEL COUNT.
- The sponge's dry weight is added to the PENDING DRY WEIGHT for use in the subsequent fluid estimate. The dry weight used is based on the COTTON, SYNTH, VAG LAP and MINI LAP selection, and on the bin where the COUNT EVENT was detected.
- If the COUNT EVENT was NOT from the user panel the LOAD SETTLING TIMER is started with a preset time of one second.
- If the source of the count was the user panel AND the count was associated with a blocked bin AND the COUNT WAIT TIMER is running, then the PENDING SPONGE WEIGHT is used to calculate an addition to the ESTIMATED SPONGE FLUID.
- If the BAG COUNT is thirty (30) or more, an audible beep is issued and all the numeric display's are set for flashing.
- If the BAG COUNT is twenty (20), an audible beep is issued and the numeric display for the count just received is set for flashing.
- When the BAG COUNT is less than thirty (<30) and not equal twenty (20) the display of all numbers is set for non-flashing.

Fluid Estimate Process

This process relies on the Disposable Interface Process for information. The LOAD EVENT indicates that there has been a change in load, the load cell has settled and a new reading is available. The new reading is the LOAD VALUE which may be used to calculate an incremental change in the estimated fluid. However, if no COUNT EVENT has been registered within the previous LOAD SETTLING TIMER period, then the new LOAD VALUE is simply saved as a new CURRENT LOAD. This allows the CURRENT LOAD to drift downward as fluid evaporates from the Disposable.

- The load change is calculated by subtracting the CURRENT LOAD from the LOAD VALUE.
- The LOAD SETTLING TIMER is checked to see if it is running. When running, this indicates that the change in load is the result of a sponge entering the Disposable.
- The LOAD SETTLING TIMER is canceled.
- If no sponge was detected and no BIN BLOCK FLAGS are set to ON, then the CURRENT LOAD is updated with the LOAD VALUE and nothing else is done by this process.
- If no sponge was detected and any BIN BLOCK FLAG is ON, then PENDING SPONGE WEIGHT is set to LOAD CHANGE and the COUNT WAIT TIMER is started with a time of three seconds. Then nothing else is done by this function.
- When the sponge was detected the PENDING DRY WEIGHT is subtracted from the LOAD CHANGE to yield the estimated fluid weight included in the LOAD CHANGE.
- This estimate is added to the ESTIMATED SPONGE FLUID and updated on the fluid display.

Load Settling Time Out Process

The LOAD SETTLING TIMER has timed out before the load cell input stabilized. The timer was started by a COUNT EVENT which has an associated fluid weight that must be registered. This function will use the LOAD VALUE to estimate the amount of fluid in question.

- The LOAD CHANGE is calculated by subtracting the CURRENT LOAD from the LOAD VALUE.
- The PENDING DRY WEIGHT is subtracted from the LOAD CHANGE to yield the estimated fluid weight included in the LOAD CHANGE.

This estimate is added to the ESTIMATED SPONGE FLUID and updated on the fluid display.

Count Wait Time Out Process

A bin has become blocked and a LOAD CHANGE was sensed indicating a possible sponge in the blocked bin. The COUNT WAIT TIMER was started to allow the operator time to enter a count on the user panel. However, the COUNT WAIT TIMER has timed out before the operator has entered the manual count. Thus the change in load will be treated as something other than a sponge. This requires that the CURRENT LOAD be updated with the new LOAD VALUE.

The CURRENT LOAD is updated with the LOAD VALUE.

Disposable Removed Process

This process is executed whenever the Disposable is removed from the device or during a power-up without the Disposable mounted. The user can identify this state by the flashing decimal pints on the count displays. During this condition the device will ignore any counts that occur. At the same time, it will accept set-up information that is properly input on the user interface panel.

Update the fluid display with the ESTIMATED SPONGE FLUID. This is zero in the case where a normal power-up up has occurred. The "Error" on the display is replaced if it was present.

Show flashing dots on all three count displays.

The CLEAR button is armed.

The COTTON, SYNTH, VAG LAP and MINI LAP buttons will have been armed only when this function is executed as a result of a power-up. If the CLEAR button is used during this function then these buttons will become armed as described in the user inputs section.

Disarm all the COUNT buttons.

Wait for DISPOSABLE MOUNTED event from Disposable Interface Process.

Error Process

Whenever the software detects a condition that will prevent the Counting and Estimating process from being properly performed the Error Process is executed. The conditions that will invoke this process are:

Power supply voltage out of acceptable range.

Load cell input invalid.

Inoperable sensor array on any bin.

Failed memory check.

Any of the above conditions will display "ERROR" on the five digit fluid display.

Disposable Interface Module

This module is concerned with the Disposable. A discrete input for DISPOSABLE MOUNTED is monitored for changes of state. The load cell analog input is averaged and compared to see if it has settled at a new value. The sensor array interface detects sponge entry and blockage.

Disposable Interface Inputs

1. IR RECEIVERS

As comprising sensors 58, an array of (preferably) infrared (IR) receivers is positioned in each bin to receive a carrier signal from IR transmitters on the opposite side of the port. Receivers from each bin are connected to input channels of the TPU, such that a signal at any bin is received at these inputs. When a carrier burst is generated at any carrier burst output channel, these inputs are sampled by the TPU for the return signal.

2. DISPOSABLE MOUNTED

When the Disposable is properly mounted on the device this discrete input is on. Changes of state on this input generate DISPOSABLE MOUNTED and DISPOSABLE DISMOUNTED events.

3. DISPOSABLE WEIGHT

The weight of the Disposable is input from a load cell with a range of zero to ten kilograms. The software reads this input from a twelve bit analog to digital converter. This resolves a measurement of one increment for every 2.44 grams.

4. MARKER SENSORS

Marker sensors, such as conventional transponder receivers, may be coupled to the process to provide input indicating identity of particular sponges or types of sponges.

Disposable Interface Outputs

1. CARRIER BURST

One CARRIER BURST signal is required for each Disposable bin. The carrier frequency is preferably 20 KHZ. A burst of carrier output preferably has a duration of three milliseconds and will begin at intervals of fifteen milliseconds. Since the software will control which bins CARRIER BURST output is in use, the return signal will be identified as to which bin it is associated.

2. DISPOSABLE EVENTS

Events originate with the Disposable Interface module and provide input to the User Interface module. Only after they are processed by the User Interface module do they affect user interface outputs.

a. COUNT EVENT

A sponge has been detected by the Disposable Interface module and it must be counted. COUNT EVENTS can be associated with any Disposable bin.

b. BLOCK EVENT

A sensor 58 or group of sensors 58 has been blocked. This event occurs when more than one of the Sensor Array inputs quit receiving pulses for a period of one second. This is sufficient time to exclude a falling sponge as the source of the sensor disturbance.

c. UNBLOCK EVENT

When a bin is blocked and carrier pulses return at all the bin's sensors for a period of three seconds, then an UNBLOCK EVENT is issued.

d. DISMOUNT EVENT

Any time that the DISPOSABLE MOUNTED input goes OFF, this event is generated. This tells the User Interface Module that the Disposable is no longer mounted properly on the device.

e. MOUNT EVENT

When the DISPOSABLE MOUNTED input goes ON this event is generated. This tells the User Interface Module that the Disposable is properly mounted and ready to accept sponges.

f. LOAD EVENT

A change in load has occurred and the load cell input has stabilized at a new value. The load settling process generates this event as it continuously reads the load cell analog input.

g. TIME-OUT EVENTS

LOAD SETTLING TIMER and COUNT WAIT TIMER are operated by the Disposable Interface Process and initiated by the User Interface Process.

Disposable Interface Processes

Sensor Process

The Sensor Process begins when the TPU is programmed to output a CARRIER BURST signal for the first bin. Since this is a known quantity of carrier pulses to the IR transmitters, the receivers can be expected to receive the same number of pulses at each IR receiver input when nothing is interrupting the IR light. Thus, the TPU received inputs are sampled during the CARRIER BURST time and checked at the completion of the burst. Any missing pulses at any of the receive inputs indicate a Detection of some kind. When nothing is detected the process proceeds to perform the same function with CARRIER BURST output for the next bin.

Detections are treated in a number of ways depending on duration and the number of receive sensors involved. Any detection of up to one second duration is a sponge entry and generates a COUNT EVENT. A detection which lasts longer than one second will generate a BLOCK EVENT. The sensor sequence is as follows:

TPU transmits CARRIER BURST for bin; simultaneously samples return signals.

Results are checked for steady state or detection. If no detection then next bin.

If detection continues for less than one second then issue COUNT EVENT

If detection continues for one second or more then a BLOCK EVENT is issued.

Load Settling Process

The load cell input is read and processed preferably ten times every second. A moving average of the input value is kept and compared to the immediate reading. When they are within one bit the input is stable. This process detects when the readings have begun changing and issues a LOAD EVENT when a return to stability is detected. The process also keeps LOAD VALUE up to date with the latest load cell reading. The sequence is as follows:

Read load cell input from ADC.

If not equal to average, set internal flag indicating that value is changing.

If equal to average and flag was set then issue LOAD EVENT.

Update LOAD VALUE available to user interface module.

Remove oldest reading from average.

Calculate new moving average.

Mounting Process

The DISPOSABLE MOUNTED input is checked ten times every second. When there is a change of state in this discrete input an event is generated for the User Interface Module. The sequence is as follows:

Read DISPOSABLE MOUNTED input.

If the input has remained in a new logic level for a half second then we have a new state.

Compare present state to previous state.

If state changed to ON then issue DISPOSABLE MOUNTED event.

If state changed to OFF then issue DISPOSABLE DISMOUNT EVENT.

Processor Management Module

This module manages the processor's resources and provides services to the User Interface and Disposable Interface Modules. Those resources include non-volatile memory and periodic timing functions for other modules. Services include start-up and self test of system, initiation of User Interface and Disposable Interface modules, historical data storage and device configuration during non-operational periods.

A Service Mode, using the serial interface, provides for device configuration and testing. This mode cannot be used during the counting and estimating process.

Processor Management Inputs

1. CPU RESET

This signal tells the CPU to start from the beginning of its program and proceed with its programmed instructions. The normal source of the RESET is a power-up of the device. However, a RESET can be forced by the watch dog timer circuit within the CPU itself. In either case, the power-up self test process is begun with a CPU RESET. Alternatively the CPU can be instructed to enter the service mode when a RESET occurs.

2. DRY WEIGHT TABLE ENTRIES

The device is configured by entering dry sponge weights into the dry weight table. See the configuration process for a description of this procedure.

Processor Management Outputs

1. HISTORICAL DATA FILE

The Historical Data file may be available for serial output any time the configuration process is being used. This file contains a record for each Disposable used and is maintained by the Historical Data Storage Process.

Processor Management Processes

Power-up, Self test and Historical Data Storage are processes used in normal operations. The Service Mode can be used at other times. The following description relates to an early model of the device, and future models may use a consistent format for Historical Data Storage and Dry Weight Table.

Power Up Self Test

Upon the application of power to the device, the software performs a device self test. The user does not see direct evidence of all the steps in the self test. However, the user does see the final results of the battery of tests performed. If any test fails to yield satisfactory results, the word 'Error' is displayed on the five digit fluid display.

After the self test, the source of the processor RESET is identified. Potential sources are Normal Power-up, Power Interruption and a Watch Dog Time-out. After the source has been identified, a memory test is performed on the standby memory, except in the case of a Power Interruption. The standby memory holds the current count, fluid and other valid information that is used to continue an operation. Doing a memory test would erase this data, making it necessary to clear and restart the device. The sequence of events during a RESET is as follows:

Read power supply voltages and check within limits.

Read load cell voltage and check for validity.

Initiate sensor array CARRIER BURST and check for valid return signal.

Illuminate all displays and LED's for three seconds.

Digit displays will show 8's to illuminate all segments.

Check status registers for Watch Dog Time-out indication.
  If this was a watch dog time-out, then record a Watch Dog Event in the historical data base.

Check for valid data in standby memory. The items that are maintained in standby memory are the fluid estimate and sponge counts for all bins. A checksum of this data is kept specifically for checking during the power-up sequence. If valid memory exists, and no Watch Doug Time-out occurred then the source of the RESET was a Power Interruption.

When the source of a RESET is not Watch Dog Time-out or Power Interruption then a Normal Power up is assumed. The standby memory is tested and initialized to zero counts and zero estimated fluid.

If any part of the self test fails, then the device will initiate the Error function. This function will display the message 'Error' on the five digit fluid display. Operation of the device will then be suspended. Otherwise the self test portion of the power-up is complete and the power-up sequence continues.

The CLEAR, COTTON, SYNTH, VAG LAP and MINI LAP buttons are armed.

DISPOSABLE MOUNTED inputs are checked to see if they indicate the Disposable is indeed mounted. If so then the software proceeds to the Counting & Estimating Process. If no Disposable is detected then the Disposable Removed process will begin.

Historical Data Storage

One record is preferably stored in non volatile memory for each Disposable used. The data may be extracted periodically by a dumb terminal or a personal computer which can be connected to the serial port on the device. This activity can only be done preferably when the unit is not being used to count sponges. Historical data recovery is a service function.

When the User Interface Module determines that a record is ready for storage, that record is transferred to the Processor Management Module. Information contained in the record is as follows:

Disposable sequence number for operation.
Type of Disposable used; two or three hole.
Type of sponges in each hole.
Count in each hole for this Disposable only.
Fluid estimate. Will include previous Disposables for operation.

As records are stored in memory they are marked as valid. When the memory fills up there is no effect on the operation of the unit. However, some device history will be lost since no more records are saved. Once the historical file has been recovered and cleared, it can begin to record data once again.

Service Process

This process will only be used when the device is not being used for the Counting and Estimating Process. To invoke this process the unit must be powered up with the service switch in the ON position. A dumb terminal connected to the unit's serial interface will be used to interact with this process. Commands can be entered on the terminal keyboard and terminated with "Enter." Responses will arrive on the terminal screen. Any command that is not understood, or contains invalid information, will cause the process to respond with three question marks ("???"). The following prompt will indicate that the configuration process is active and waiting for a command.

SPONGETRAC>

Configuration Commands

The Configuration Process will be used for two things: (1) to view and change dry weights for all types of sponges that can be selected and (2) to recover unit historical data which will have been save over a period of time.

Table Command

This command will be used to view the table of dry sponge weights that is being used by the software. The command TABLE followed by "Enter" will show the table as shown in the example below. The table display includes some reference numbers that will be used in the CHANGE command below. Bin numbers correspond to the disposable bins numbered from left to right when facing the disposable. Column numbers (Col.) are provided to reference the type of sponge selections that the user interface provides for.

Format: TABLE
Example Response:

|   |        | COTTON | SYNTH | COTTON | SYNTH | COTTON | SYNTH |
|---|--------|--------|-------|--------|-------|--------|-------|
|   |        |        |       | COTTON/SYNTH REG/VAG LAP/MINI LAP | | | |
|   |        | REG    | REG   | VAG LAP | VAG LAP | MINI LAP | MINI LAP |
| 1 | Left   | 3.6    | 3.6   | —      | —     | 12.0   | 12.0  |
| 2 | Center | 0.0    | 0.0   | —      | —     | —      | —     |
| 3 | Right  | 20.8   | 20.8  | 13.4   | 13.4  | 12.0   | 12.0  |
| ^Bin Col > | | 1 | 2 | 3 | 4 | 5 | 6 |

Change Command

Any dry weight in the table will be changed by using the CHANGE command. This command has three parameters that must be included as in the example below. The BIN# is a number from one through three to indicate the bin as shown in the table. The COL# is a number from one through 6 as shown by the table. The New Weight is the actual dry weight in grams that is being entered into the table. All three parameters are checked for their valid range. The range of values acceptable for New Weight is from zero up to and including 99.9 grams.

Format: CHANGE bin#,col#,New Weight
Example: CHANGE 3,5,11.5

This example changes the dry weight for the right bin(3), when cotton mini sponges(5) are selected to a value of 11.5 grams.

HFILE Command: Recover Historical Data File

This command requests all the records from the device historical data file. There is one record in the file for each disposable used since the file was last cleared. Or, if the file is full, one record for each disposable used until the file was filled. No more records are recorded once the file is full. One line of text is output for each record in the file. Each line includes all the fields in the record separated by comma's.

Format: HFILE
Example Response:
1,2,1,1,5,15,0,11,1243
2,2,1,1,5,21,0,18,2897
3,2,1,1,5,5,0,14,3679
1,3,2,2,4,7,26,1,795

Breaking down the first record in the example: Each field represents information about the use of one disposable. Records can be separated into groups of fields as below.

| Seq # | Disposable Type* | Sponge Types | Counts | Est. Fluid |
|---|---|---|---|---|
| 1, | 2, | 1,1,5 | 15,0,11, | 1243 |

The first number (1) is the Disposable Sequence number. In the example three Disposables are used in one operation. The first has the sequence number 1, then 2, and so on.

The next number (2) is the type of Disposable used. A two hole disposable in this case.

The next three numbers (1,1,5) are the types of sponges selected by the user for each hole. The record shows cotton selected and mini lap sponges for the right bin. These numbers correspond with the COL# from the dry weight table.

The next three numbers (15,0,11) in the record are the BAG COUNTS for each bin of that disposable. Notice that the center bin is zero when the disposable had two holes.

The final number is the ESTIMATED SPONGE FLUID for the operation including previous Disposables. Notice that this number grows with each sequence number in an operation.

HCLEAR Command

This command clears the historical data file in the device. It can be used after the data has been successfully recovered with the HFILE command.

Format: HCLEAR

HCOUNT Command

Request the current historical counts for each type of disposable. The software keeps a count of Disposables used for each type of Disposable. These counts go from zero to 99999 before they roll over. The first number is for two hole Disposables and the second number for the three hole Disposable count. The third number is the number of Watch Dog Time-outs that have occurred since the last HCLEAR command. This will be important information to service personnel if it is ever anything but zero.

Format: HCOUNT

Example Response: 23456, 1099, 0

Test Commands

These commands are used to test parts of the hardware. They are intended to assist factory testing by giving the test technician access to the various parts of the system. Several commands have parameters associated with them. In the commands described below, the keyword of the command is in all capitals with parameters following in lower case. All parameters will be entered in hexadecimal characters.

Button Report

This command waits for indication from the panel button detect hardware that a button was pressed. A single character is sent to the serial port to represent each button pressed. Hexadecimal characters representing the sixteen possible codes from the button hardware will be used. Any input character from the serial port will cancel the test.

Format BUTTON

Example Response: 01F

Display Data

This command sends data to a one of the numeric displays on the user panel. The display number and data are included in the command parameters. Display updates occur repeatedly when this command is entered until a subsequent character is received at the serial port. Valid display numbers are 1 through 4. Configuration is one byte and data is three bytes.

| Format | DISP display # configuration data |
|---|---|
| Example | DISP 01 F0 801234 |

Ad Sample

This command repeatedly samples an analog input channel with a specified delay between samples. Each input value is transmitted as one line of information which will appear as a column of numbers on the terminal screen. The numbers will be in decimal with a range of zero to 65535. Delay is a time value in milliseconds. Valid channel numbers are 0 through 7. Any character received will cancel this function.

| Format | | AD channel # delay |
|---|---|---|
| Example | AD 1 3F | |
| | | 10456 |
| | | 10567 |
| | | 10567 |

Mounted State

This command repeatedly monitors the state of the DISPOSABLE MOUNTED input and reports its condition. A delay time is entered to be used between input samples. Each result is reported with a single character. A period is used when the input is off and an 'X' when the input is on indicated a disposable in place. Any input character from the serial port will cancel the test.

| Format | | MS delay |
|---|---|---|
| Example | MS IF | |
| | | ....X......XXXXX |

Bin Sensor Test

Any bin can be individually tested with this command. The TPU is setup for a burst of carrier pulses according to the parameters entered. The TPU receive channels are checked for the proper receive data. The report to the terminal is a string of ten characters representing the ten receive channels. A dot indicates no detection and an 'X' represents a detection, which means one or more pulses were missing on the receive channel. The process is repeated after the delay time until a character is received on the serial channel to cancel the test.

Valid bin numbers are 1 and 2. Offset1 and Offset2 are the high and low times of the carrier pulses respectively. These are expressed in number of TPU clock cycles which is 4 MHZ. The loopcount is the number of pulses to include in the burst. The delay is in milliseconds and includes the time of the burst.

| Format | BIN bin # offset1 offset2 loopcount delay |
|---|---|
| Example | BIN 01 64 64 3C 0F |
| | . . . X . . . . . . |

```
        .   X  X  X   .   .   .   .
        X   X  X  X   .   .   .   .
        X   X  X  X   X   .   .   .
        X   X  X  X   .   .   .   .
    X   X   X  X  .   .   .   .   .
    X   X   X  .  .   .   .   .   .
        X   .  .  .   .   .   .   .
```

Memory Tests

Memory tests are available for each type of memory in the system. The test numbers are one through four. Test one is a destructive test of the standby system ram. Test two is a destructive test of the data ram. Test three verifies the checksums for the EPROMS in the system. Test four is used to test the non volatile EPROM in the system. Test four will destroy any historical data that has been recorded as well as the system dry weight table.

| Format | MEM test # |
|---|---|
| Example | MEM 01 |

Low Voltage Input Test

This test sets up the interrupt used for early power fail and then waits for the interrupt to occur. Upon an interrupt the message "F" is sent to the terminal screen. Any character entered cancels the test.

| Format |    | LV |
|---|---|---|
| Example | LV |    |
|    |    | F |

Beep Test

This test produces an audible beep as used for warning purposes. The audible output is turned on and held until a subsequent character is received.

| Format | BEEP |
|---|---|

Watchdog Timer Test

This test enables the watchdog timer feature in the MC68332 and waits for it to rest the CPU. If the RESET occurs then the system will return to its prompt. If not any character entered will cancel the test.

| Format | WATCH |
|---|---|

Read Configuration Switches

This command reads and reports the state of the four configuration switches on the CPU board. A one or zero is displayed for each switch.

| Format |    | CSW |
|---|---|---|
| Example | CSW |    |
|    |    | 0101 |

Other features and modifications may be employed with tracking device according to the present invention. It may, for instance, be utilized with items other than sponges and surgical procedures. Additionally programming according to the above-disclosed data flow and functional sequence disclosure may occur using any desirable language and on any desirable processor and memory components. Communications modules may be added to allow for remote data transfer, quality assurance monitoring or other purposes. It will be apparent that other modifications may occur without departing from the scope or spirit of this invention.

What is claimed is:

1. Apparatus for tracking articles, comprising:
   a. at least one disposable container which contains at least one retention section for retaining articles which have been placed in the container, and at least one port through which the articles may be introduced;
   b. at least one load cell adapted to determine the weight of the articles;
   c. structure adapted to suspend the container from the load cell in a manner that places the load imposed by the container and the articles on the load cell;
   d. a plurality of optical sensors corresponding to each port, adapted to sense passage of articles through the port;
   e. processor means and memory means adapted to receive input signals from the load cell and the optical sensors in order to calculate weight and counts of the articles; and
   f. a display for displaying cumulative weights and cumulative counts of the articles.

2. Apparatus according to claim 1 in which the container further comprises a receptacle which contains the retention sections and a top member connected to the receptacle, which top member contains at least one port, and which top member is adapted to be borne by the apparatus structure.

3. Apparatus according to claim 2 in which the container further comprises an optical region adapted to permit at least partial passage of energy emitted by the sensors through the container in order to sense the presence of articles.

4. Apparatus according to claim 1 in which the optical sensors are adapted to detect energy emitted by photodiodes.

5. Apparatus according to claim 1 in which the load cell comprises a parallelogram-like structure that includes two substantially vertical members connected flexibly to two substantially horizontal members, one of which vertical members is connected to the container and a transducer for imparting a signal to the processor means corresponding to the deformation of the transducer, and the other of which vertical members is connected to the apparatus.

6. Apparatus according to claim 1 further comprising means for sensing presence of identity markers in the articles, which sensing means are coupled to the processor and memory means.

7. Apparatus for tracking articles, comprising:
   a. at least one disposable container which contains at least one retention section for retaining articles which have been placed in the container, and at least one port through which the articles may be introduced into the retention section;
   b. at least one load cell adapted to determine the weight of the articles, which load cell comprises a parallelogram-like structure that includes two substantially vertical members connected flexibly to two substantially horizontal members, one of which vertical members is connected to the container and a transducer for imparting a signal to the processor means corresponding to the deformation of the transducer, and the other of which vertical members is connected to the apparatus;
   c. structure adapted to suspend the container from the load cell in a manner that places the load imposed by the container and the articles on the load cell;

d. a plurality of optical sensors corresponding to each port, adapted to sense passage of articles through the port;

e. at least one identity sensor for detecting identity markers attached to the articles;

f. processor means and memory means adapted to receive input signals from the load cell, the optical sensors and the identity sensors in order to calculate weight and counts of the articles; and g. a display for displaying cumulative weights and counts of the articles.

8. Apparatus according to claim 7 in which the container further comprises a receptacle which contains the retention sections and a top member connected to the receptacle, which top member contains the ports, and which top member is adapted to be borne by the apparatus structure.

9. Apparatus according to claim 7 in which the container further comprises an optical region adapted to permit at least partial passage of energy emitted by the sensors through the container in order to sense the presence of articles.

10. Apparatus for tracking articles, comprising:

a. at least one disposable container featuring at least one port through which the articles may be introduced into the container;

b. at least one load cell adapted to determine the weight of the articles;

c. structure adapted to suspend the container from the load cell in a manner that places the load imposed by the container and the articles on the load cell;

d. a plurality of optical sensors that correspond to each port, adapted to sense passage of articles through the port;

e. processor means and memory means adapted to receive input signals from the load cell and the optical sensors in order to calculate weight and counts of the articles, which processor and memory means contain means for allowing the load cell to settle before weight is registered; and f. a display for displaying cumulative volumes received from cumulative weights and cumulative counts of the articles.

11. Apparatus according to claim 10 in which the container comprises a receptacle having retention sections, each corresponding to a port.

12. Apparatus according to claim 10 in which the optical sensors are photodiodes which emit energy in bursts.

13. Apparatus according to claim 10 which further comprises means for detecting blockages in at least one of the ports and issuing a notification of such a blockage.

14. Apparatus for tracking articles, comprising:

a. at least one disposable container which includes a receptacle featuring at least one retention section for retaining articles which have been placed in the container, and a top member sorting grid which contains at least one port through which the articles may be introduced into the retention sections and which is adapted to be borne by structure of the apparatus;

b. at least one load cell adapted to determine the weight of the articles which load cell comprises a parallelogram-like structure that includes two substantially vertical members connected flexibly to two substantially horizontal members, one of which vertical members is connected to the container and a transducer for imparting a signal to the processor means corresponding to the deformation of the transducer, and the other of which vertical members is connected to the apparatus;

c. structure adapted to suspend the container from the load cell in a manner that places the load imposed by the container and the articles on the load cell;

d. a plurality of sensors corresponding to each port, adapted to sense passage of articles through the port;

e. processor means and memory means adapted to receive input signals from the load cell and the sensors in order to calculate weight and counts of the articles; and f. a display for displaying cumulative weights and counts of the articles.

15. Apparatus according to claim 14 in which the container further comprises at least one region for permitting passage of at least part of the energy emitted by the sensors.

16. Apparatus according to claim 14 in which the sensors emit and sense energy in the infrared region of the electromagnetic spectrum.

17. Apparatus according to claim 14 in which the sensors emit and sense visible light.

18. Apparatus according to claim 14 in which the sensors include photodiodes.

19. Apparatus according to claim 14 in which the top member is adapted to seal the container in fluid tight fashion.

20. Apparatus according to claim 14 in which the structure adapted to suspend the container from the load cell in a manner that places the load imposed by the container and the articles on the load cell includes at least one member cantilevered from one of the vertical members of the load cell and adapted to receive portions of the container.

21. Apparatus according to claim 14 further comprising identity sensor means for sensing presence of identity markers in the articles, which identity sensor means is coupled to the processor and memory means.

22. Apparatus for tracking articles, comprising:

a. at least one disposable container for receiving the articles;

b. at least one load cell adapted to determine the weight of the articles, which load cell comprises structure connected to the apparatus and to the container, and coupled to the processor and memory means, which structure is adapted to constrain loads imparted by the container and the articles to act and to be sensed only in a substantially vertical direction;

c. structure adapted to suspend the container from the load cell in a manner that places the load imposed by the container and the articles on the load cell;

d. a plurality of sensors adapted to sense passage of articles into the container;

e. processor means and memory means adapted to receive input signals from the load cell and the sensors in order to calculate weight and counts of the articles; and f. a display for displaying cumulative weights and counts of the articles.

23. Apparatus according to claim 22 in which the load cell structure includes a parallelogram-like structure that includes two substantially vertical members connected flexibly to two substantially horizontal members, one of which vertical members is connected to the container and a transducer for imparting a signal to the processor means corresponding to the deformation of the transducer, and the other of which vertical members is connected to the apparatus.

24. Apparatus according to claim 22 in which the vertical members are connected to the horizontal members via hinge connections.

25. Apparatus according to claim 22 in which the transducer is mounted on an s-shaped substrate, one end of which is attached to the apparatus and one end of which is attached to one of the vertical members of the load cell.

26. A container for receiving and retaining articles, and adapted to be employed in connection with apparatus for tracking the articles, which apparatus includes at least one load cell for determining the weight of the container and the articles, and sensors adapted to sense presence of the articles within the container, which container comprises:

a. a receptacle formed of plastic, nonrigid, material, which includes at least one retention section, each for retaining a separate version of article;

b. a top member which is at least quasi-rigid, which is connected to the receptacle and adapted to be borne by structure of the apparatus so that the container is suspended from the load cell, and which includes at least one port corresponding to a retention section of the receptacle; and c. a region contained in the receptacle which permits passage of at least a portion of the energy emitted by the sensors to penetrate the receptacle for sensing the presence of the articles.

27. A container according to claim 26 further comprising a cover connected to the top member for sealing the container.

28. A container according to claim 26 further comprising a cover connected to the top member for sealing the container in fluid-tight fashion.

29. A container according to claim 26 which is adapted to be closed and sealed in a manner that acceptably prevents escape of biohazardous materials.

30. A container according to claim 26 further comprising a defining member within the receptacle which, when the container is deployed within the structure of the apparatus, lends shape to the receptacle.

31. A container according to claim 26 further comprising an entry port in the receptacle for access to at least some of the articles, which entry port may be resealed in liquid-tight fashion.

32. A container according to claim 26 in which the receptacle includes at least four walls and a bottom connected to the walls, which walls taper inward toward the bottom so that the area defined by a cross section through the four walls at the bottom is smaller than a cross section through the four walls at the top of the receptacle.

33. A container for receiving and retaining articles, and adapted to be employed in connection with apparatus for tracking the articles, which apparatus includes at least one load cell for determining the weight of the container and the articles, and sensors adapted to sense presence of the articles within the container, which container comprises:

a. a receptacle which includes a plurality of walls formed of flexible plastic material that define at least one retention section, each retention section adapted to receive and retain a version of article different than that retained in other retention sections, and the walls tapering inward toward the bottom of the receptacle to ease deployment of the container in the apparatus;

b. a top member connected to the receptacle, which is adapted in size and shape to be borne by structure of the apparatus, which contains at least one port, each corresponding to a retention section of the receptacle;

c. a region in the container adapted to allow at least partial passage of energy emitted by the optical sensors through the container; and d. a cover connected to the top member for sealing the container.

34. A container according to claim 33 further comprising a defining member contained in the receptacle for imparting shape to the receptacle when it is deployed in the apparatus.

35. A container according to claim 33 in which the sealing member is adapted to seal the container in fluid-tight fashion.

36. A container according to claim 33 further comprising an entry port in at least one wall of the receptacle for allowing access to at least some of the articles in the container, and which is adapted to be resealed in fluid tight fashion.

37. Apparatus for tracking articles, comprising:

a. at least one disposable container which contains at least one retention section for retaining articles which have been placed in the container, and at least two ports through which the articles may be introduced into the retention sections;

b. at least one load cell adapted to determine the weight of the articles;

c. structure adapted to suspend the container from the load cell in a manner that places the load imposed by the container and the articles on the load cell;

d. a plurality of sensors corresponding to each port, adapted to sense passage of articles through the port;

e. processor means and memory means adapted to receive input signals from the load cell and the sensors in order to calculate weight and counts of the articles, which processor is adapted to track (1) presence or absence of the container on the suspension structure in order to account for articles in a succession of containers; (2) input from the load cell; (3) input from at least one table containing information relating to dry weight of articles and containers; (4) input from the sensors and (5) input from buttons adapted to control operation of the apparatus; and to correlate information from the load cell and the sensors in order to track various types of articles contained in the container; and f. a display for displaying cumulative weights and counts of the articles.

38. Apparatus according to claim 37 in which the sensors include light emitting diodes adapted to emit energy in pulses under control of the processor means.

39. Apparatus according to claim 37 further comprising an interface for manual input of information into the processor and memory means.

40. Apparatus according to claim 39 further comprising an interface for manually incrementing and decrementing article counts tracked by the apparatus.

41. A process for tracking counts of articles placed in a container and weights of materials in the articles, comprising, for each additional article, the steps of:

a. detecting passage of the article into the container using an optical sensor;

b. incrementing an article count display coupled to the optical sensor;

c. sampling input from a load cell, which supports the container, the weight of the container;

d. when the load cell input changes, averaging the input until the average stabilizes to a Load Value;

e. referring to a table which contains empty weight of the articles to find a Pending Dry Weight for the article;

f. subtracting the Pending Dry Weight from the Load Value to estimate a new Estimated Article Contents Value;

g. displaying the Estimated Article Contents Value;

h. storing the Load Value as a Current Load Value prior to the time that the load cell input changes;

i. when the load cell input changes, averaging the input until the average stabilizes to a New Load Value;

j. subtracting the Current Load Value from the New Load Value to estimate a Load Change Value;

k. subtracting the Pending Dry Weight from the Load Change Value in order to estimate an increment to the Estimated Article Contents Value; and l. adding the increment of Estimated Article Contents Value to the Estimated Article Contents Value.

42. A process according to claim 41 further comprising the step of not calculating Estimated Article Contents Value until a predetermined Time Out period has passed.

43. A process according to claim 41 further comprising the step of interrupting the processes in the optical sensors sense that entrance to the container is blocked.

44. A process according to claim 41 further comprising the steps of storing the displayed counts and Estimated Article Contents Value when the container is removed, interrupting the process until a replacement container is added, and continuing the process when the new container is added.

45. A process according to claim 41 further comprising the step of issuing an audible notification when the article count on the display reaches a predetermined value.

46. A process according to claim 41 in which the articles pass through one of at least one port in the container, and their passage into the container is sensed by a set of optical sensors corresponding to the port through which they pass.

* * * * *

UNITED STATES PATENT AND TRADEMARK OFFICE
CERTIFICATE OF CORRECTION

PATENT NO. : 5,629,498
DATED : May 13, 1997
INVENTOR(S) : Richard A. Pollock

It is certified that error appears in the above-indentified patent and that said Letters Patent is hereby corrected as shown below:

Column 19, line 25, delete "up" second occurrence

Column 23, line 6, delete "Doug" and insert --Dog--

Signed and Sealed this

Thirtieth Day of June, 1998

*Attest:*

BRUCE LEHMAN

*Attesting Officer*     *Commissioner of Patents and Trademarks*